United States Patent [19]
Seela et al.

[11] Patent Number: 6,066,720
[45] Date of Patent: May 23, 2000

[54] MODIFIED OLIGONUCLEOTIDES, THEIR PREPARATION AND THEIR USE

[75] Inventors: Frank Seela, Osnabrück; Sigrid Lampe, Berge/Hekese, both of Germany

[73] Assignee: Hoechst Aktiengesellschaft, Frankfurt am Main, Germany

[21] Appl. No.: 09/094,405

[22] Filed: Jun. 10, 1998

Related U.S. Application Data

[62] Division of application No. 08/940,196, Sep. 29, 1997, Pat. No. 5,789,562, which is a continuation of application No. 08/431,777, May 1, 1995, abandoned.

[30] Foreign Application Priority Data

May 2, 1994 [DE] Germany .............................. 44 15 370

[51] Int. Cl.⁷ .............................. C12Q 1/68; C07H 19/00; C07H 21/00; A01N 61/00
[52] U.S. Cl. .............................. 536/22.1; 435/6; 435/91.1; 435/91.2; 514/1; 514/44; 536/23.1; 536/24.3; 536/25.3; 536/25.32; 536/27.1; 536/27.11; 536/27.12; 536/27.13
[58] Field of Search .............................. 435/6, 91.1, 91.2; 514/1, 44; 536/22.1, 23.1, 24.3, 25.3, 25.32, 27.1, 27.11, 27.12, 27.13

[56] References Cited

U.S. PATENT DOCUMENTS

| 4,711,955 | 12/1987 | Ward et al. .............................. 536/29 |
| 5,268,464 | 12/1993 | Brill ...................................... 536/25.3 |
| 5,594,121 | 1/1997 | Froehler et al. ........................ 536/23.5 |
| 5,789,562 | 8/1998 | Seela et al. ............................. 536/22.1 |

FOREIGN PATENT DOCUMENTS

| 0 552 766 | 7/1993 | European Pat. Off. . |
| WO92/ 02258 | 7/1991 | WIPO . |
| WO/93 10820 | 11/1992 | WIPO . |

OTHER PUBLICATIONS

E. Uhlmann et al., "Antisense Oligonucleotides: A New Therapeutic Principle," Chemical Reviews, vol. 90, No. 4, Jun. 1990, pp. 544–584.
J. F. Milligan, "Current Concepts in Antisense Drug Design," Journal of Med. Chemistry, vol. 36, No. 14, Jul. 1993, pp. 1923–1937.
H. Inoue et al., "Synthesis and hybridization of dodecadeoxyribonucleotides containing a fluorescent pyridopyrimidine deoxynucleoside," Nucleic Acids Research, vol. 13, No. 19 (1985), pp. 7119–7129.
Andre Chollet et al., "DNA containing the base analogue 2–aminoadenine: preparation, use as hybridization probes and cleavage by restriction endonucleases," Nucleic Acids Research, vol. 16, No. 1 (1988), pp. 305–317.
E. Sonveaux, "The Organic Chemistry Underlying DNA Synthesis", Bioorganic Chemistry 14, (1986), pp. 274–325.

Serge L. Beaucage et al., "Advances in the Synthesis of Oligonucleotides by the Phosphoramidite Approach," Tetrahedron Report No. 309, vol. 48, No. 12, pp. 2223–2311 (1992).
Louis J. Ravin, Ph.D., "Preformulation," Pharmaceutical Preparations and Their Manufacture, Part 8, pp. 1409–1423.
J. Ludwig, "A New Route to Nucleoside 5'–triphosphates," Acta Biochim. et Biophys. Acad. Sci. Hung., vol. 16 (3–4), pp. 131–133 (1981).
D. Grunberger et al., Synthesis and Coding Properties of 8–Azaguanosine–Containing Triribonucleoside Diphosphates, Biochimica et Biophysica Acta 161, (1968), pp. 147–155.
John. W. Bodnar et al., "Effect of Nucleotide Analogs on the Cleavage of DNA by the Restriction Enzymes AluI, DdeI, HinfI, RsaI, and TaqI*," The Journal of Biological Chemistry, vol. 258, No. 24, pp. 15206–15213 (1983).
Frank Seela et al., "8–Aza–2'–deoxyguanosine and Related 1,2,3–Triazolo[4,5–d]pyrimidine 2'–Deoxyribofuranosides, Separatum Helvetica Chimica Acta," vol. 76, pp. 2388–2397 (1993).
L. J. McBride et al., "N⁶(N–Methyl–2–Pyrrolidine Amidine) Deoxyadenosine—A New Deoxynucleoside Protecting Group," Tetrahedron Letters, vol. 24, No. 29, pp. 2953–2956 (1983).
G. S. Ti et al., "Transient Protection: Efficient One–Flask Syntheses of Protected Deoxynucleosides," J. Am. Chem. Soc., vol. 104, pp. 1316–1319 (1982).
H. Schaller et al., "Studies on Polynucleotides, XXIV, The Stepwise Synthesis of Specific Deoxyribopolynucleotides (4). Protected Derivatives of Deoxyribonucleosides and New Syntheses of Deoxyribonucleoside–3' Phosphates," J. Chem. Soc. vol. 85, No. 34 (1963), pp. 3821–3825.
Colin B. Reese, "The Chemical Synthesis of Oligo– and Polycarboxylic acid–Nucleotides by the Phosphotriester Approach," Tetrahedron Report No. 56, vol. 34, pp. 3143–3179.
Deiter Flockerzi et al., "Synthesis and Properties of 2'–0– and 3'–0–(tert–Butyldimethylsilyl)–5'–0–(40methoxytrityl)–'and 2',3'–Bis(O–tert–butyldimethylsilyl) ribonucleosides—Starting Materials for Oligoribo–nucleotide," Liebigs Ann. Chem. (1981), pp. 1568–1585.
Brian C. Froehler et al., "Synthesis of DNA via deoxynucleoside H–phosphonate intermediates," Nucleic Acid Research, vol. 14, No. 13, (1986) pp. 5399–5407.

(List continued on next page.)

Primary Examiner—Jezia Riley
Attorney, Agent, or Firm—Finnegan, Henderson, Farabow, Garrett & Dunner, L.L.P.

[57] ABSTRACT

The invention relates to novel modified oligonucleotides which contain at least one 8-azapurine base and form more stable hybridization complexes with nucleic acids; To a process for their preparation, and to their use as inhibitors of gene expression, as probes for detecting nucleic acids, as aids in molecular biology, and as a pharmaceutical or diagnostic agent.

19 Claims, No Drawings

OTHER PUBLICATIONS

N. D. Sinha et al., "Polymer support oligonucleotide synthesis XVIII: Use of B–cyanoethyl–N,N–dialkylamino–/N–morpholino phosphoramidite of deoxynucleosides for the synthesis of DNA fragments simplifying deprotection and isolation of the final product," Nucleic Acids Rsearch, vol. 12, No. 11 (1984), pp. 4539–4557.

Frank Seela et al., "7 Deazaadenosine: Oligoribonucleotide Building Block Synthesis and Autocatalytic Hydrolysis of Base–Modified Hammerhead Ribozymes," Helvetica Chemica Acta, vol. 76 (1993) pp. 1809–1820.

Nassim Usman et al., "Preparation of Ribonucleoside 3'–0–Phosphoramidites and Their Application to the Automated Solid Phase Synthesis of Oligo–nucleotides," Tetrahedron Letters, vol. 26, No. 38, pp. 4567–4570 (1985).

Masakazu Koga et al., "Alternating ^a,β–Oligothymidylates with Alternating (3'–>3')—and (5'–>5')—Internucleotidic Phosphodiester Linkages as Models for Antisensse Oligodeoxyribonucleotides," The Journal of Organic Chemistry, vol. 56, No. 12, pp. 3757–3759 (1991).

Collection Of Czechoslovak Chemical Communications, D. Grünberger, et al., "Synthesis of Triribonucleoside Diphosates With Ribonuclease $T_1$," vol. 33, (1968), pp. 286–295.

Journal of Heterocyclic Chemisty, S. Tono–oka et al., "Enzymatic ADP–Ribosylation of Benzotriazoles and Related Triazoles. Difference of Glycosidation Site Between Triazoles and Indazoles," vol. 26, No. 2, (1989); pp. 339–343.

Biochemistry, B. G. Hughes, et al., "2',5'–Oligoadenylates and Related 2',5'–Oligonucleotide Analogues. 1. Substate Specificity of Interferon–Induced Murine 2',5'–Oligoadenylate Synthetase and Enzymatic Synthesis of Oligomers," vol. 22, No. 9, (1983); pp. 2116–2126.

Helvetica Chimica Acta, F. Seela et al., "94. Synthesis, Base Pairing, and Structural Transitions of Oligodeoxyribonucleotides Containing 8–Aza–2'–deoxyguanosine," vol. 77, No. 4, (1994); pp. 1003–1017.

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: HIV (ix) FEATURE:
        (A) NAME/KEY: exon
        (B) LOCATION: 1..20

(xi) SEQUENCE DESCRIPTION: SEQ ID NO: 1:

ACACCCAATT CTGAAAATGG                                              20

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: HIV (ix) FEATURE:
        (A) NAME/KEY: exon
        (B) LOCATION: 1..20

(xi) SEQUENCE DESCRIPTION: SEQ ID NO: 2:

AGGTCCCTGT TCGGGCGCCA                                              20

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: HIV (ix) FEATURE:
        (A) NAME/KEY: exon
        (B) LOCATION: 1..28

(xi) SEQUENCE DESCRIPTION: SEQ ID NO: 3:

GTCGACACCC AATTCTGAAA ATGGATAA                                   28

(2) INFORMATION FOR SEQ ID NO: 4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: HIV (ix) FEATURE:
        (A) NAME/KEY: exon
        (B) LOCATION: 1..25

(xi) SEQUENCE DESCRIPTION: SEQ ID NO: 4:

GCTATGTCGA CACCCAATTC TGAAA                                             25

(2) INFORMATION FOR SEQ ID NO: 5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: HIV (ix) FEATURE:
        (A) NAME/KEY: exon
        (B) LOCATION: 1..31

(xi) SEQUENCE DESCRIPTION: SEQ ID NO: 5:

TCGTCGCTGT CTCCGCTTCT TCTTCCTGCC A                                      31

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: HIV (ix) FEATURE:
        (A) NAME/KEY: exon
        (B) LOCATION: 1..31

(xi) SEQUENCE DESCRIPTION: SEQ ID NO: 6:

CTGTCTCCGC TTCTTCTTCC TGCCATAGGA G                                      31

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: HSV-1

(ix) FEATURE:
        (A) NAME/KEY: exon
        (B) LOCATION: 1..20

(xi) SEQUENCE DESCRIPTION: SEQ ID NO: 7:

GCGGGGCTCC ATGGGGGTCG        20

(2) INFORMATION FOR SEQ ID NO: 8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: human (ix) FEATURE:
        (A) NAME/KEY: exon
        (B) LOCATION: 1..15
        (D) OTHER INFORMATION: /note= "c-Ha-ras"

(xi) SEQUENCE DESCRIPTION: SEQ ID NO: 8:

CAGCTGCAAC CCAGC        15

(2) INFORMATION FOR SEQ ID NO: 9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: human (ix) FEATURE:
        (A) NAME/KEY: exon
        (B) LOCATION: 1..21
        (D) OTHER INFORMATION: /note= "c-myc"

(xi) SEQUENCE DESCRIPTION: SEQ ID NO: 9:

GGCTGCTGGA GCGGGGCACA C        21

(2) INFORMATION FOR SEQ ID NO: 10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: human (ix) FEATURE:
        (A) NAME/KEY: exon
        (B) LOCATION: 1..15
        (D) OTHER INFORMATION: /note= "c-myc"

(xi) SEQUENCE DESCRIPTION: SEQ ID NO: 10:

AACGTTGAGG GGCAT                              15

(2) INFORMATION FOR SEQ ID NO: 11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: human (ix) FEATURE:
        (A) NAME/KEY: exon
        (B) LOCATION: 1..15
        (D) OTHER INFORMATION: /note= "c-myb"

(xi) SEQUENCE DESCRIPTION: SEQ ID NO: 11:

CACGTTGAGG GGCAT                              15

(2) INFORMATION FOR SEQ ID NO: 12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: human (ix) FEATURE:
        (A) NAME/KEY: exon
        (B) LOCATION: 1..18
        (D) OTHER INFORMATION: /note= "c-myb"

(xi) SEQUENCE DESCRIPTION: SEQ ID NO: 12:

```
GTGCCGGGGT CTTCGGGC                                                        18

(2) INFORMATION FOR SEQ ID NO: 13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: Mous (ix) FEATURE:
        (A) NAME/KEY: exon
        (B) LOCATION: 1..18
        (D) OTHER INFORMATION: /note= "c-myb"

(xi) SEQUENCE DESCRIPTION: SEQ ID NO: 13:

GTGTCGGGGT CTCCGGGC                                                        18

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: human (ix) FEATURE:
        (A) NAME/KEY: exon
        (B) LOCATION: 1..21
        (D) OTHER INFORMATION: /note= "c-fos"

(xi) SEQUENCE DESCRIPTION: SEQ ID NO: 14:

GGAGAACATC ATGGTCGAAA G                                                    21

(2) INFORMATION FOR SEQ ID NO: 15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: human (ix) FEATURE:
        (A) NAME/KEY: exon
        (B) LOCATION: 1..22
        (D) OTHER INFORMATION: /note= "c-fos"
```

(xi) SEQUENCE DESCRIPTION: SEQ ID NO: 15:

CCCGAGAACA TCATGGTCGA AG                                                         22

(2) INFORMATION FOR SEQ ID NO: 16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: YES (vi) ORIGINAL SOURCE:
            (A) ORGANISM: human (ix) FEATURE:
            (A) NAME/KEY: exon
            (B) LOCATION: 1..20
            (D) OTHER INFORMATION: /note= "c-fos"

(xi) SEQUENCE DESCRIPTION: SEQ ID NO: 16:

GGGGAAAGCC CGGCAAGGGG                                                            20

(2) INFORMATION FOR SEQ ID NO: 17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: YES (vi) ORIGINAL SOURCE:
            (A) ORGANISM: human (ix) FEATURE:
            (A) NAME/KEY: exon
            (B) LOCATION: 1..20
            (D) OTHER INFORMATION: /note= "p-120"

(xi) SEQUENCE DESCRIPTION: SEQ ID NO: 17:

CACCCGCCTT GGCCTCCCAC                                                            20

(2) INFORMATION FOR SEQ ID NO: 18:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: YES (vi) ORIGINAL SOURCE:
            (A) ORGANISM: human (ix) FEATURE:
            (A) NAME/KEY: exon
            (B) LOCATION: 1..18

(D) OTHER INFORMATION: /note= "EGF-Rezeptor"

(xi) SEQUENCE DESCRIPTION: SEQ ID NO: 18:

GGGACTCCGG CGCAGCGC                                                 18

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
         (A) ORGANISM: human (ix) FEATURE:
         (A) NAME/KEY: exon
         (B) LOCATION: 1..20
         (D) OTHER INFORMATION: /note= "EGF-Rezeptor"

(xi) SEQUENCE DESCRIPTION: SEQ ID NO: 19:

GGCAAACTTT CTTTTCCTCC                                               20

(2) INFORMATION FOR SEQ ID NO: 20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
         (A) ORGANISM: human (ix) FEATURE:
         (A) NAME/KEY: exon
         (B) LOCATION: 1..19
         (D) OTHER INFORMATION: /note= "p53 Tumorsuppressor"

(xi) SEQUENCE DESCRIPTION: SEQ ID NO: 20:

GGGAAGGAGG AGGATGAGG                                                19

(2) INFORMATION FOR SEQ ID NO: 21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
         (A) ORGANISM: human (ix) FEATURE:

(A) NAME/KEY: exon
        (B) LOCATION: 1..21
        (D) OTHER INFORMATION: /note= "p53 Tumorsuppressor"

(xi) SEQUENCE DESCRIPTION: SEQ ID NO: 21:

GGCAGTCATC CAGCTTCGGA G                                                         21

(2) INFORMATION FOR SEQ ID NO: 22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: human (ix) FEATURE:
        (A) NAME/KEY: exon
        (B) LOCATION: 1..18
        (D) OTHER INFORMATION: /note= "cdc2-Kinase"

(xi) SEQUENCE DESCRIPTION: SEQ ID NO: 22:

GTCTTCCATA GTTACTCA                                                             18

(2) INFORMATION FOR SEQ ID NO: 23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: human (ix) FEATURE:
        (A) NAME/KEY: exon
        (B) LOCATION: 1..18
        (D) OTHER INFORMATION: /note= "PCNA (proliferating cell
            nuclear antigen)"

(xi) SEQUENCE DESCRIPTION: SEQ ID NO: 23:

GATCAGGCGT GCCTCAAA                                                             18

(2) INFORMATION FOR SEQ ID NO: 24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:

(A) ORGANISM: human (ix) FEATURE:
        (A) NAME/KEY: exon
        (B) LOCATION: 1..18
        (D) OTHER INFORMATION: /note= "VLA-4"

(xi) SEQUENCE DESCRIPTION: SEQ ID NO: 24:

GCAGTAAGCA TCCATATC                                                     18

(2) INFORMATION FOR SEQ ID NO: 25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: human (ix) FEATURE:
        (A) NAME/KEY: exon
        (B) LOCATION: 1..20
        (D) OTHER INFORMATION: /note= "ICAM"

(xi) SEQUENCE DESCRIPTION: SEQ ID NO: 25:

CCCCCACCAC TTCCCCTCTC                                                   20

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
        (A) ORGANISM: human (ix) FEATURE:
        (A) NAME/KEY: exon
        (B) LOCATION: 1..20
        (D) OTHER INFORMATION: /note= "ICAM"

(xi) SEQUENCE DESCRIPTION: SEQ ID NO: 26:

CTCCCCCACC ACTTCCCCTC                                                   20

(2) INFORMATION FOR SEQ ID NO: 27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: YES (vi) ORIGINAL SOURCE:
             (A) ORGANISM: human (ix) FEATURE:
             (A) NAME/KEY: exon
             (B) LOCATION: 1..19
             (D) OTHER INFORMATION: /note= "ICAM"

(xi) SEQUENCE DESCRIPTION: SEQ ID NO: 27:

GCTGGGAGCC ATAGCGAGG                                                    19

(2) INFORMATION FOR SEQ ID NO: 28:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iii) ANTI-SENSE: YES (vi) ORIGINAL SOURCE:
             (A) ORGANISM: human (ix) FEATURE:
             (A) NAME/KEY: exon
             (B) LOCATION: 1..21
             (D) OTHER INFORMATION: /note= "ELAM-1"

(xi) SEQUENCE DESCRIPTION: SEQ ID NO: 28:

ACTGCTGCCT CTTGTCTCAG G                                                 21

(2) INFORMATION FOR SEQ ID NO: 29:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iii) ANTI-SENSE: YES (vi) ORIGINAL SOURCE:
             (A) ORGANISM: human (ix) FEATURE:
             (A) NAME/KEY: exon
             (B) LOCATION: 1..22
             (D) OTHER INFORMATION: /note= "ELAM-1"

(xi) SEQUENCE DESCRIPTION: SEQ ID NO: 29:

CAATCAATGA CTTCAAGAGT TC                                                22

(2) INFORMATION FOR SEQ ID NO: 30:

(i) SEQUENCE CHARACTERISTICS:
             (A) LENGTH: 12 base pairs
             (B) TYPE: nucleic acid
             (C) STRANDEDNESS: single
             (D) TOPOLOGY: linear (ii) MOLECULE TYPE: DNA (iii) HYPOTHETICAL: YES

```
    (iii) ANTI-SENSE: YES (ix) FEATURE:
         (A) NAME/KEY: -
         (B) LOCATION: 1..11
         (D) OTHER INFORMATION: /note= "N = 8-Azaguanin"

(xi) SEQUENCE DESCRIPTION: SEQ ID NO: 30:

GTANAATTCT AG                                                      12
```

MODIFIED OLIGONUCLEOTIDES, THEIR PREPARATION AND THEIR USE

This is a division of application Ser. No. 08/940,196, filed Sep. 29, 1997, now U.S. Pat. No. 5,789,562 which is a continuation application of application Ser. No. 08/431,777, filed May 1, 1995, now abandoned.

The present invention relates to novel oligonucleotides which contain modified bases and which possess valuable physical, biological and pharmacological properties, to a process for their preparation, and to their use as inhibitors of gene expression (antisense oligonucleotides, ribozymes, sense oligonucleotides and triplex-forming oligonucleotides), as probes for detecting nucleic acids, as aids in molecular biology, and as a pharmaceutical or a diagnostic agent.

Numerous chemical modifications of oligonucleotides are known from the literature. These modifications can affect the sugar-phosphate skeleton or the nucleotide bases. Reviews of the state of the art are provided, for example, by Uhlmann & Peyman, Chem. Rev. 1990, 90 543 and Milligan et al., J. Med. Chem. 1993, 36, 1923.

As a rule, it is necessary to modify the oligonucleotides chemically, since unmodified oligonucleotides are very rapidly degraded by nucleolytic activities both in cells and in cell culture medium. Stabilization against nucleolytic degradation can be achieved by replacing the sugar-phosphate backbone, or by modifying the phosphate bridge, the sugar component or the nucleotide base [Milligan et al., see above, and Uhlmann & Peyman, see above].

In addition to modifications which lead to oligonucleotides which have increased stability towards nucleolytic degradation modifications are also of interest which alter the hybridization behavior of the modified oligonucleotides such that these oligonucleotides are able, for example, to form more stable hybridization complexes (duplexes) with intracellular nucleic acid (so-called target nucleic acids). It is possible to alter the hybridization properties of oligonucleotides by, for example, modifying their bases. The altered hybridization properties of such modified oligonucleotides can be recognized, for example, by the fact that the melting temperature ($T_m$ value) of the duplexes is altered as compared with when unmodified oligonucleotides are used.

Thus, PCT Application WO 92/002258 describes pyrimidine-modified oligonucleotides which, however, exhibit a decreased rather than an increased binding affinity for single-stranded and double-stranded target nucleic acids. However, PCT Application WO 93/10820 also discloses oligonucleotides which contain modified uracil bases and cytosine bases and which can form duplex or triplex structures with the target nucleic acids which are more stable than those achieved using non-modified oligonucleotides. The hybridization properties of synthetic dodecamer oligonucleotides which contain the base analog pyridopyrimidine have also been investigated [Inoue et al. (1985), Nucleic Acid Res., 13, 7119–7129]. Oligonucleotides which contain the base analog 2-aminoadenine have also been reported to have improved hybridization properties [Chollet et al., (1988), Nucleic Acid Research, 16, 305–317].

The object of the present invention is, therefore, to make available novel oligonucleotides which possess advantageous properties.

It has now been found, surprisingly, that oligonucleotides which contain at least one 8-aza-purine base, for example 8-azaguanine or 8-azaadenine, form hybridization complexes with the target nucleic acids which are markedly more stable than those formed by comparable oligonucleotides which contain the unmodified purine bases.

The invention thus relates to oligonucleotides of the formula I

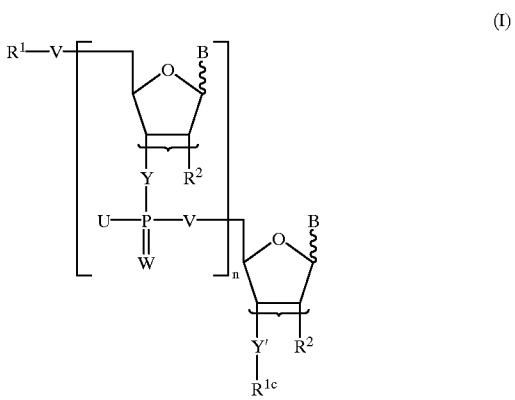

(I)

and the physiologically tolerated salts thereof, in which $R^1$ is hydrogen, $C_1$–$C_{18}$-alkyl, $C_2$–$C_{18}$-alkenyl, $C_2$–$C_{18}$-alkynyl, $C_2$–$C_{18}$-alkylcarbonyl, $C_3$–$C_{19}$-alkenylcarbonyl, $C_3$–$C_{19}$-alkynylcarbonyl, ($C_6$–$C_{14}$)-aryl-($C_1$–$C_8$)-alkyl, a protective group which is customary in nucleotide chemistry, or a radical of the formula IIa

(IIa)

$R^{1a}$ is hydrogen, $C_1$–$C_{18}$-alkyl, $C_2$–$C_{18}$-alkenyl, $C_2$–$C_{18}$-alkynyl, $C_2$–$C_{18}$-alkylcarbonyl, $C_3$–$C_{19}$-alkenylcarbonyl, $C_3$–$C_{19}$-alkynylcarbonyl, ($C_6$–$C_{14}$)-aryl-($C_1$–$C_8$)-alkyl, or a radical of the formula IIb

(IIb)

$R^2$ is hydrogen, hydroxyl, $C_1$–$C_{18}$-alkoxy, $C_1$–$C_6$-alkenyloxy, in particular allyloxy, halogen, azido or $NH_2$;

a is oxy or methylene;

n is an integer from 3 to 99;

W is oxo, thioxo or selenoxo;

V is oxy, sulfanediyl or imino;

Y is oxy, sulfanediyl, imino or methylene;

Y' is oxy, sulfanediyl, imino, $(CH_2)_m$ or $V(CH_2)_m$, in which m is an integer from 1 to 18;

X is hydroxyl or mercapto;

U is hydroxyl, mercapto, SeH, $C_1$–$C_{18}$-alkoxy, $C_1$–$C_{18}$-alkyl, $C_6$–$C_{20}$-aryl, ($C_6$–$C_{14}$)-aryl-($C_1$–$C_8$)-alkyl, $NHR^3$, $NR^3R^4$ or a radical of the formula III

$(OCH_2CH_2)_pO(CH_2)_qCH_2R^5$     (III)

in which
- $R^3$ is $C_1$–$C_{18}$-alkyl, $C_6$–$C_{20}$-aryl, ($C_6$–$C_{14}$)-aryl-($C_1$–$C_8$)-alkyl, or 2-$(CH_2)_c$—$[NH(CH_2)_c]_d$—$NR^6R^6$, in which c is an integer from 2 to 6 and d is an integer from 0 to 6, and $R^6$ are, independently of each other, hydrogen or $C_1$–$C_6$-alkyl or $C_1$–$C_4$-alkoxy-$C_1$–$C_6$-alkyl;
- $R^4$ is $C_1$–$C_{18}$-alkyl, $C_6$–$C_{20}$-aryl or ($C_6$–$C_{10}$)-aryl-($C_1$–$C_8$)-alkyl, or, in the case of $NR^3R^4$, is, together with $R^3$ and the nitrogen atom carrying them, a 5-6-membered heterocyclic ring which can additionally contain a further heteroatom from the group O, S and N,
- p is an integer from 1 to 100,
- q is an integer from 0 to 22,
- $R^5$ is hydrogen or a functional group such as, for example, hydroxyl, amino, $C_1$–$C_{18}$-alkylamino, COOH, $CONH_2$, $COO(C_1$–$C_4)$-alkyl or halogen;
- Z and Z' are, independently of each other, hydroxyl, mercapto, SeH, $C_1$–$C_{22}$-alkoxy, —O—$(CH_2)_b$—$NR^6R^7$, in which b is an integer from 1 to 6, and $R^7$ is $C_1$–$C_6$-alkyl, or $R^6$ and $R^7$, together with the nitrogen atom carrying them, form a 3-6-membered ring, $C_1$–$C_{18}$-alkyl, $C_6$–$C_{20}$-aryl, ($C_6$–$C_{14}$)-aryl-($C_1$–$C_8$)-alkyl, ($C_6$–$C_{14}$)-aryl-($C_1$–$C_8$)-alkoxy, where aryl is also heteroaryl, and aryl is optionally substituted by 1, 2 or 3 identical or different radicals from the group carboxyl, amino, nitro, $C_1$–$C_4$-alkylamino, $C_1$–$C_6$-alkoxy, hydroxyl, halogen and cyano, $C_1$–$C_{18}$-alkylmercapto, $NHR^3$, $NR^3R^4$, a radical of the formula III or a group which favors intracellular uptake or which serves as the label of a DNA probe, or, when the oligonucleotide analog hybridizes to the target nucleic acid, attacks the latter with binding, crosslinking or cleavage, and the curved bracket, indicates that $R^2$ and the adjacent phosphoryl radical can be located either in the 2' and 3' positions or else, conversely, in the 3' and 2' positions, where each nucleotide can be present in its D or L configuration and the base B can be located in the α or β position, where
- B are independently of each other, a base which is customary in nucleotide chemistry, for example natural bases such as adenine, cytosine, thymine, guanine, uracil or hypoxanthine, or unnatural bases such as, for example, purine, 8-azapurine, 2,6-diaminopurine, 7-deazaadenine, 7-deazaguanine, $N^4N^4$-ethanecytosine, $N^6N^6$-ethano-2,6-diaminopurine, pseudoisocytosine, 5-methylcytosine, 5-fluorouracil, 5-($C_3$–$C_6$)-alkynyluracil, 5-($C_3$–$C_6$)-alkynylcytosine, or their prodrug forms, where at least one B is a base of the formula IV

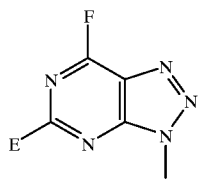

(IV)

in which E and F are, independently of each other, H, OH or $NH_2$.

Compounds of the fomula I are preferred, in which E is $NH_2$ and F is OH, or E is H and F is $NH_2$. Compounds of the formula I are particularly preferred in which E is $NH_2$ and F is OH. Compounds of the formula I are also preferred in which the base is located in the β position on the sugar, the nucleosides are present in the D configuration, $R^2$ is located in the 2' position and a is oxy.

When attached to complementary nucleic acids (target nucleic acids), the novel oligonucleotides exhibit a binding affinity which is improved as compared with that exhibited by the natural oligonucleotides. If these novel oligonucleotides are to be used therapeutically, it is advantageous if additional modifications, for example of the phosphate backbone, the ribose unit or the oligonucleotide ends, are introduced into them [J. S. Cohen, Topics in Molecular and Structural Biology 12 (1989) Macmillan Press, E. Uhlmann et al., see above]. For example, the novel oligonucleotides are protected even more effectively against nuclease attack, which is advantageous, if modifications, which are known per se, are made to their sugar-phosphate backbone.

Compounds of the formula I are also preferred, therefore, in which V, Y, Y' and W have the meaning of thioxo, selenoxo, oxy, oxo, sulfanediyl, imino or methylene, and U has the meaning of hydroxyl, mercapto or methyl. The latter compounds are very particularly preferred if $R^2$ is also hydroxyl or hydrogen, in particular hydrogen.

Compounds of the formula I in which $R^1$ and $R^{1a}$ are hydrogen also represent a preferred embodiment.

Compounds of the formula I are very particularly preferred in which $R^1$ and/or $R^{1a}$ is/are hydrogen, $R^2$ is hydroxyl or hydrogen, U is hydroxyl or mercapto and V, Y, Y' and W have the meaning of thioxo, oxy, oxo or hydroxyl.

Protective groups which are customary in nucleotide chemistry are understood to mean, for example, amino protective groups, hydroxyl protective groups or other protective groups, as described in [E. Sonveaux, 1986, Bioorganic Chemistry, 14, 274–325 or S. L. Beaucage et al., 1992, Tetrahedron, 48, 2223–2311].

Alkyl, alkenyl or alkynyl can be straight-chain or branched.

Cycloalkyl is also understood to mean alkyl-substituted rings.

Examples of ($C_6$–$C_{20}$)-aryl are phenyl, naphthyl or biphenyl, preferably phenyl.

Heteroaryl is understood to mean, in particular, radicals which are derived from phenyl or naphthyl and in which one or more CH groups are replaced by N, and/or in which at least two adjacent CH groups are replaced by S, NH or O (with the formation of a five-membered aromatic ring). In addition, one or both atoms of the condensation site of bicyclic radicals can be N atoms (as in indolizinyl).

Furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl are, in particular, regarded as heteroaryl.

Physiologically tolerated salts of compounds of the formula (I) are understood to be both inorganic and organic salts, as described in Remington's Pharmaceutical Sciences (17th edition, page 4181 (1985)).

For reasons of physical and chemical stability, and solubility, sodium salts, potassium salts, calcium salts and ammonium salts, inter alia, are preferred for acid groups.

The invention is not limited to α- and β-D- and L-ribofuranosides, α- and β-D- and L-deoxyribofuranisides and corresponding carbocyclic five-membered ring analogs, and, instead, also applies to oligonucleotide analogs which are constructed from other sugar building blocks, for example xylofuranose and arabinofuranose derivatives, ring-expanded and ring-contracted sugars, acyclic or ringbridged sugar derivatives, or suitable sugar derivatives of another type. Furthermore, the invention is not limited to the derivatives of the phosphate radical which are given by way of example in formula I, and, instead, also relate to the known dephospho derivatives.

The novel oligonucleotides can, consequently, be derived by modifying the natural structure in a wide variety of ways. Examples of these modifications, which can be introduced by methods which are known per se, are:

a) Modifications of the phosphate bridge

The following may be mentioned by way of example: phosphorothioates, phosphorodithioates, methyl phosphonates, phosphoramidates, boranophosphates, methyl phosphates, ethyl phosphates and phenyl phosphonates. Phosphorothioates, phosphorodithioates and methyl phosphonates are preferred modifications of the phosphate bridge.

b) Replacement of the phosphate bridge

The following may be mentioned by way of example: replacement with formacetal, 3'-thioformacetal, methylhydroxylamine, oxime, methylenedimethylhydrazo, dimethylenesulfone or silyl groups. Replacement with formacetals and 3'-thioformacetals is preferred.

c) Modifications of the sugar

The following may be mentioned by way of example: α-anomeric sugars, 2'-O-methylribose, 2'-O-butylribose, 2'-O-butylribose, 2'-O-allylribose, 2'-fluoro-2'-deoxyribose, 2'-amino-2'-deoxyribose and α-arabinofurose, and carbocyclic sugar analogs. The preferred modification is that with 2'-O-methylribose and 2'-O-n-butylribose.

d) Modifications of the sugar and of the phosphate bridge

The peptide nucleic acids (PNAs), in which the sugar/phosphate backbone is replaced by an aminoethylglycine backbone, and also the carbamate-bridged morpholino oligomers, may be mentioned by way of example.

e) Other modifications of the bases, in particular of the pyrimidine bases

The following may be mentioned by way of example: 5-propynyl-2'-deoxyuridine, 5-propynyl-2'-deoxycytidine, 5-hexynyl-2'-deoxyuridine, 5-hexynyl-2'-deoxycytidine, 5-fluoro-2'-deoxycytidine, 5-fluoro-2'-deoxyuridine, 5-hydroxymethyl-2'-deoxyuridine, 5-methyl-2'-deoxycytidine and 5-bromo-2'-deoxycytidine. 5-Propynyl-2'-deoxyuridin, 5-hexynyl-2'-deoxyuridine, 5-hexynyl-2'-deoxycytidine and 5-propynyl-2'-deoxycytidine are preferred modifications.

f) 3'-3' inversions and 5'-5' inversions [e.g. M. Koga et al., J. Org. Chem. 56 (1991) 3757 ]

g) 5'conjugates and 3'conjugates.

Examples of groups which favor intracellular uptakes are different lipophilic radicals such as —O—$(CH_2)_x$—$CH_3$, in which x is an integer from 6 to 18, —O—$(CH_2)_n$—CH=CH—$(CH_2)_m$—$CH_3$, in which n and m, indepedently of each other, are an integer from 6 to 12, —O—$(CH_2CH_2O)_4$—$(CH_2)_9$—$CH_3$, —O—$(CH_2CH_2O)_8$—$(CH_2)_{13}$—$CH_3$ and —O—$(CH_2CH_2O)_7$—$(CH_2)_{15}$—$CH_3$, and also steroid residues such as cholesteryl, or vitamin residues such as vitamin E, vitamin A or vitamin D, and other conjugates which exploit natural carrier systems, such as cholic acid, folic acid, 2-(N-alkyl, N-alkoxy)-aminoanthraquinone and conjugates of mannose, and peptides of the corresponding receptors which lead to receptor-mediated endocytosis of the oligonucleotides, such as EGF (epidermal growth factor), bradykinin and PDGF (platelet-derived growth factor). Labeling groups are understood to mean fluorescent groups, for example of dansyl (=N-dimethyl-1-aminonaphthyl-5-sulfonyl) derivatives, fluorescein derivatives or coumarin derivatives, or chemiluminescent groups of, for example, acridine derivatives, and also the digoxygenin system, which can be detected by way of ELISA, the biotin group which can be detected by way of the biotin/avidin system, or else linker arms having functional groups which permit subsequent derivatization with detectable reporter groups, for example an amino-alkyl linker which is reacted with an active acridinium ester to form a chemiluminescent probe. The following are typical labeling groups:

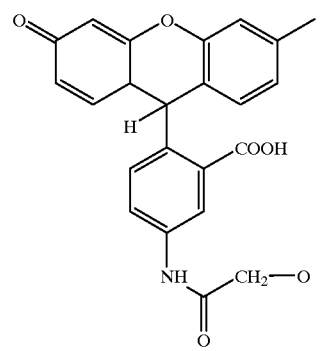

Fluorescein derivative

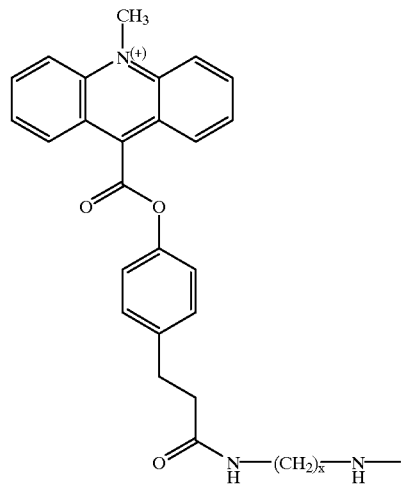

Acridinium ester

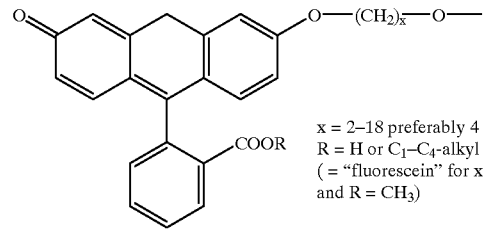

x = 2–18 preferably 4
R = H or $C_1$–$C_4$-alkyl
( = "fluorescein" for x = 4 and R = $CH_3$)

Fluorescein derivative

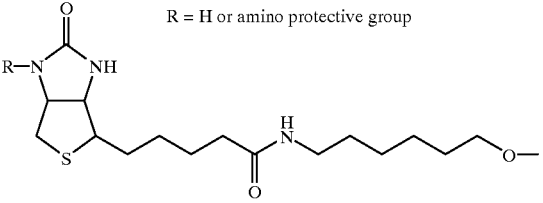

R = H or amino protective group

Biotin conjugate ( = "biotin" for R = Fmoc)

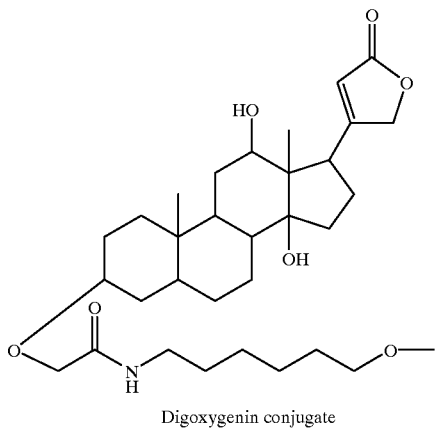

Digoxygenin conjugate

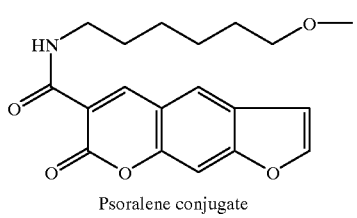

Psoralene conjugate

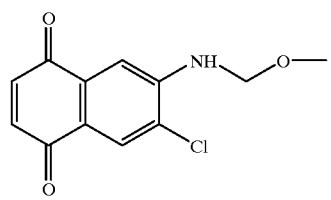

Naphthoquinone conjugate

Oligonucleotide analogs which bind to or intercalate with nucleic acids and/or cleave or crosslink them contain, for example, conjugates of acridine, psoralene, phenanthridine, naphthoquinone, daunomycin or chloroethylaminoaryl. Typical intercalating and crosslinking residues are:

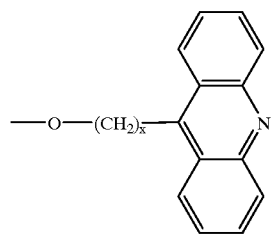

Acridine derivative x = 2–12, preferably 4

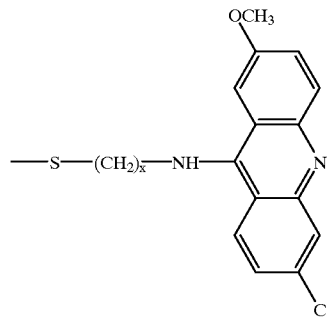

x = 2–12, preferably 4

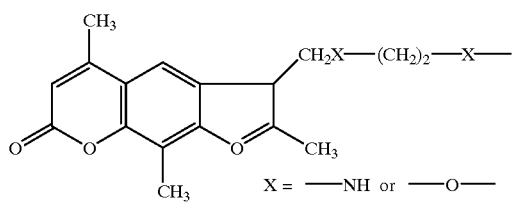

Trimethylpsoralene conjugate ( = "psoralene" for X = O)

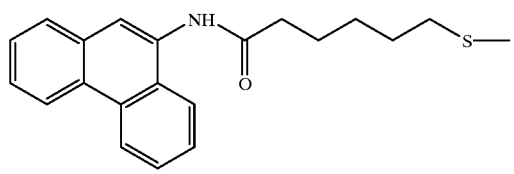

Phenanthroline conjugate

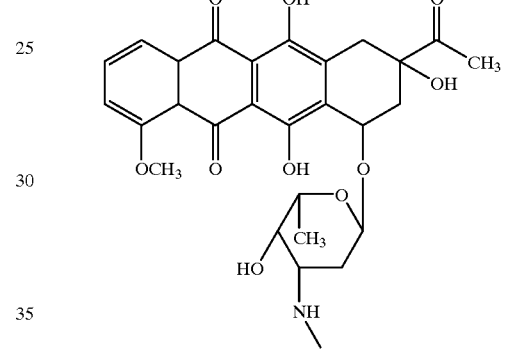

Daunomycin derivative

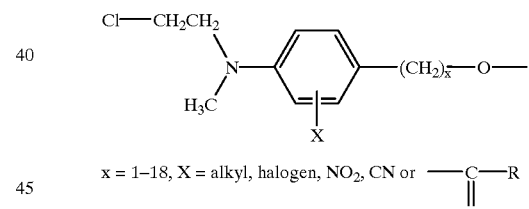

x = 1–18, X = alkyl, halogen, $NO_2$, CN or —C(=O)—R

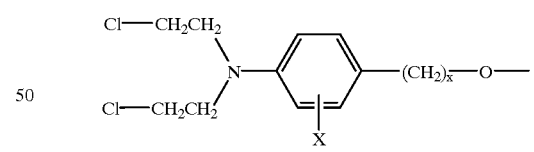

x = 1–18, X = alkyl, halogen, $NO_2$, CN or —C(=O)—R

Examples of $NR^3R^4$ groups, in which $R^3$ and $R^4$, together with the nitrogen atom carrying them, form a 5- or 6-membered heterocyclic ring which additionally contains a further heteroatom, which may be mentioned are the morpholinyl residue and imidazolidinyl residue.

The invention furthermore relates to the compound of the formula V

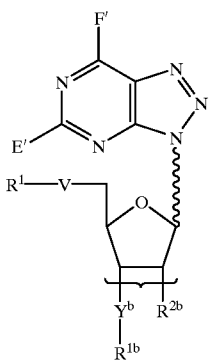

(V)

in which

V is oxy, sulfanediyl or imino;

$Y^b$ is oxy, sulfanediyl, imino or methylene;

a is oxy or methylene;

$R^{2b}$ is hydrogen, $OR^{12}$, $C_1$–$C_{18}$-alkoxy, $C_1$–$C_6$-alkenyloxy, in particular allyloxy, halogen, azido or $NR^{10}R^{11}$;

$R^1$ is a protective group which is customary in nucleotide chemistry;

$R^{1b}$ is a radical of the formula IIc and IId

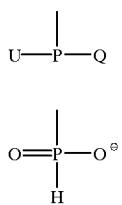

(IIc)

(IId)

in which

U is O-$R^7$ or S-$R^7$;

Q is a radical —$NR^8R^9$, $R^7$ is —$(CH_2)_2$—CN;

$R^8$ and $R^9$ are identical or different and are $C_1$–$C_6$-alkyl, in particular isopropyl or ethyl, or, together with the nitrogen atom carrying them, are a 5–9-membered heterocyclic ring which can additionally contain a further heteroatom from the group O, S and N, in particular

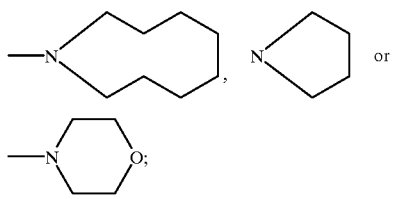

E' and F' are, independently of each other, H, OH, or $NR^{10}R^{11}$, $R^{10}$ and $R^{11}$ are identical or different and are hydrogen or an amino protective group which is customary in nucleotide chemistry, or $R^{10}$ and $R^{11}$ together form an amino protective group which is customary in nucleotide chemistry, $R^{12}$ is a hydroxyl protective group which is customary in nucleotide chemistry, such as, for example, t-butyldimethylsilyl, triisoproopylsily, o-nitrobenzyl, p-nitrobenzyl, tris(1-methylethyl)silyl or 2-fluorophenyl-4-methoxypiperidin-4-yl (FPMP), and the curved bracket indicates that $R^2$ and the adjacent phosphoryl radical can be in the 2' and 3' positions or else, conversely, in the 3' and 2' positions.

Compounds of the formula (V) in which V, $Y^b$ and a are oxy, $R^{2b}$ is hydrogen or $OR^{12}$, in particular hydrogen, and $R^{1b}$ is a radical of the formula (IIc) or (IId), where U is O—$(CH_2)_2$—CN and $R^8$ and $R^9$ are identical or different and are isopropyl or ethyl, represent a preferred embodiment.

These compounds are very particularly preferred if, in addition, the base on the sugar is in the β position and $R^{2b}$ is in the 2' position.

The invention also relates to compounds of the formula V in which linkage to the sugar residue takes place by way of the N2 atom of the 8-azapurine base.

Examples of preferred amino protective groups are acyl protective groups or amidine protective groups.

The invention also relates to compounds of the formula VI

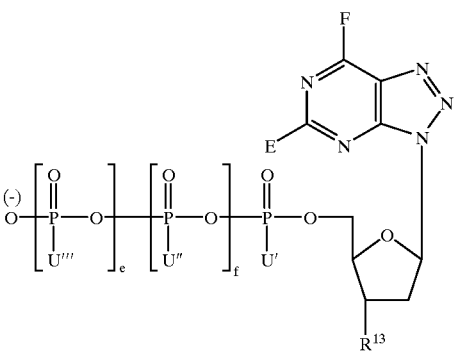

(VI)

in which, independently of each other,

U'=U''=U''' is hydroxyl or merapto;

e and f are 0 or 1;

$R^{13}$ is hydrogen or OH, and

E and F H, OH or $NH_2$, where compounds of the formula VI are excepted in which U', U'', U''', $R^{13}$ and F are OH, E is $NH_2$ and e and f are 1.

Compounds of the formula VI are preferred in which U' is hydroxyl or mercapto, U''=U''' is hydroxyl, and e and/or f is/are 1.

In addition, compounds of the formula VI are preferred in which

E is H, and F is $NH_2$, or, if E is $NH_2$, and F is OH, $R^{13}$ is H, or, if, E is $NH_2$, and F, $R^{13}$, R', U'' and U''' are OH, then e and/or f is/are 0, or, if E is $NH_2$, and F, $R^{13}$, U'' and R''' are OH, and e and f are 1, then U'is mercapto.

The novel compounds of the formula VI can be employed as aids in molecular biology, for example in PCR reactions (e=f=1, $R^{13}$=OH) or for sequencing (e=f=1; $R^{13}$=H or OH).

The compounds of the formula VI can be prepared from the corresponding 8-azapurine nucleosides using generally known methods. The compounds of the formula VI may preferably be prepared using an abbreviated version of Ludwig's one pot process in the presence of 1,8-bis- (dimethylamino)naphthalene and trimethyl phosphate [J. Ludwig et al., (1981) Acta Biochem. Biophys. Sci. Hung., 16, 131].

The invention also embraces all the tautomeric forms of the compounds of the formulae I, V and VI, in particular all the tautomeric forms of the 8-azapurine bases of the formula IV.

The invention furthermore relates to a process for preparing the novel compounds of the formula I.

Grünberger et al. [Biochim., Biophys. Acta, (1968) 161, 147–155] have described the preparation of triribonucleoside diphosphates containing 8-azaguanine by an enzymic or chemoenzymic route. Bodnar et al. describe the enzymic synthesis of double-stranded, 8-azaguanine-containing phage DNA using DNA polymerase [Bodnar et al., (1983) J. Biol. Chem., 258, 15206–15213].

Owing to the fact that the N-glycosidic bond of 8-azadeoxyguanosine is extremely stable to acid [Seela et al., (1993), Helv. Chim, Acta, 76, 2388–2397], the standard conditions which are customary in the chemical synthesis of oligonucleotides may be employed for preparing the novel 8-azapurine-containing oligonucleotides.

The novel compounds of the formula I are prepared in solution or, preferably, on a solid phase, where appropriate using an apparatus for automatic synthesis. The construction of the oligomers of formula I can take place stepwise by condensing mononucleotides, in each case containing a nucleotide base, one at a time, onto an appropriately derivatized support or onto a growing oligomer chain.

The oligonucleotide is constructed using the methods known to the person skilled in the art, such as the triester method, the H-phosphonate method or the phosphoramidite method [E. Sonveaux, (1986), Bioorganic Chemistry, 14, 274–325; S. L. Beaucage et al., (1992), Tetrahedron, 48, 2223–2311]. The nucleotide monomer building blocks of the formula V are preferably employed for introducing the 8-azapurine derivatives, with those nucleotide monomers of the formula V in which E' is $NR^{10}R^{11}$ and F' is OH being particularly preferred.

The compounds of the formula V, as building blocks for the oligonucleotide solid phase synthesis, can be prepared from the corresponding 8-asapurine nucleosides. Once appropriate protective groups for the amino groups of the 8-azapurine bases and the free 5'-hydroxyl group of the sugar have been introduced, the monomers are converted into the corresponding phosphonate or phosphoramidite derivatives. Suitable amino protective groups, for example in the form of a formamidine protective group ((dimethylamino)methylidene) or acyl protective group, are introduced using generally known methods [L. J. McBride et al, (1983) Tetrahedron Lett., 24, 2953, G. S. Ti et al, (1982) J. Am. Chem. Soc., 104, 1316; H Schaller et al. (1963), J. Am. Chem. Soc., 85, 3821], with the use of Schaller's peracylation method being advantageous when the amino group is acylated. An example of a suitable protective group for the free 5'-OH group of the sugar is 4,4'- dimethoxytrityl, which is likewise introduced using known methods [C. B. Reese (1978), Tetrahedron, 34, 3143; D. Flockerzi et al., (1981), Leibigs Ann. Chem., 1568]. The monomers which have been protected in this way can be converted to the corresponding phosphonates using a protocol developed by Froehler et al., [B. C. Froehler et al., (1986), Nucl. Acid Res., 14, 5399]. Cyanoethylphophoramidite derivatives can be prepared, for example, by reacting the monomers with chloro-β- cyanoethyoxy(N,N-diisoopropylamino) phosphane in anhydrous dischloromethane [N. D. Sinha et al., (1984) Nucl. Acid Res., 12, 4539].

The oligoribonucleotide synthesis is rendered more difficult, as compared wit the deoxyribooligonucleotide synthesis, as a result of the additional 2'-OH group. The first difficulty is that of finding a combination of compatible 2'-OH and 5'-OH protective groups. Thus, during the oligonucleotide synthesis, the residue at the O-2' position has to be stable towards the acid conditions used for hydrolysing the trityl protective groups. In addition, conditions have to be avoided which could lead to migration of the phosphate radical from the 3' position to the 2' position. A regioselective reaction is desirable when introducing the protective group.

It is advantageous for synthesizing the novel oligoribonucleotides of the formula (I) to use triisopropylsilyl chloride as the 2'-OH protective group, with which high degrees of selectivity are achieved in association with adequate stability and mild elimination conditions (TBAF/THF). The selectivity of the reaction can be increased still further if silver nitrate is used as the catalyst in place of imidazole [F. Seela, K. Mersmann, J. A. Grasby, M. J. Gait, Helv. Chim. Acta 1993, 76, 1809].

In contrast to the situation as regards the solid phase synthesis of deoxyribonucleotides, phosphoramidite building blocks are not particularly suitable for the solid phase synthesis of oligoribonucleotides. This is due, in particular, to relatively long coupling times being required as a result of the reactive phosphoramidite being sterically hindered by the bulky 2'-silyl protective group [N. Usman, R. T. Pon, K. K. Ogilvie, Tetrahedron Lett. 1985, 26, 4567], which hinderance also results in a lower coupling yield. Ribonucleoside phosphonates are more stable towards hydrolysis and oxidation than are the phosphoramidites and permit the oligonucleotide synthesis to take place with relatively short cycling times.

The ribonucleotide phosphonates according to the invention may be prepared using a protocol developed by Froehler [B. Froehler, P. G. Nug, M. D. Mateuci, Nucl. Acids Res. 1986, 14, 5399].

Compounds of the formula I whose oligonucleotide moieties are modified at the 3' and/or 5' ends are synthesized, with respect to these modifications, using the methods described in EP-A 0 552 766.

The invention also relates to the use of the novel compounds of the formula I for preparing a pharmaceutical, and also to a process for preparing a pharmaceutical which comprises mixing the novel oligonucleotides with a physiologically acceptable excipient and also, where appropriate, suitable additives and/or auxiliary substances.

In a quite general manner, the present invention extends to the use of compounds of the formula I as therapeutically active components of a pharmaceutical. In general, therapeutically active oligonucleotide derivatives are understood to mean antisense oligonucleotides, triple helix-forming oligonucleotides, aptamers or ribosomes, in particular antisense oligonucleotides.

In addition to this, the present invention also relates to the use of oligonucleotides containing at least one 8-asapurine, preferably containing 8-azaguanine or 8-aza-adenine, as a diagnostic agent, for example for detecting the presence of absence, or the quantity, of a specific double-stranded or single-stranded nucleic acid molecule in a biological sample.

For being used in accordance with the invention, the oligonucleotides have a length of from 4 to 100, preferably of approximately 5–40, in particular of approximately 6–30, nucleotides. Apart from that, the abovedescribed preference ranges, modifications and conjugations also apply in this instance.

The pharmaceuticals of the present invention can be used, for example, for treating diseases which are elicited by viruses, for example by HIV, HSV-1, HSV-2, influenza, VSV, hepatitis B or papilloma viruses.

Novel antisense oligonucleotide derivatives, that is antisense oligonucleotides in which at least one purine base is replaced by an 8-azapurine base, and which are active against targets of this nature, have the following base sequences, for example:

oligonucleotide sequences can be employed in this context which are directed against targets which are responsible for the appearance and growth of cancers. Examples of such targets are:

1) Nuclear oncoproteins such as, for example, c-myc, N-myc, c-myb, c-fos, c-fos/jun, PCNA and p120

2) Cytoplasmic/membrane-associated oncoproteins such as, for example, EJ-ras, c-Ha-ras, N-ras, rrg, bcl-2, cdc-2, c-raf-1, c-mos, c-scr and c-abl 3) Cellular receptors, such as, for example, EGF receptor, c-erbA, retinoid receptors, protein kinase regulatory subunit and c-fms 4) Cytokines, growth factors and extracellular matrix, such as, for example, CSF-1, IL-6, IL-1a, IL-1b, IL-2, IL-4, bfGF, myeloblastin and fibronectin.

Novel antisense oligonucleotides of the formula I which a) against HIV, e.g.

5'-A C A C C C A A T T C T G A A A A T G G-3' (SEQ. ID. No. 1) or
(I)

5'-A G G T C C C T G T T C G G G C G C C A-3' (SEQ. ID. No. 2) or
(II)

5'-G T C G A C A C C C A A T T C T G A A A A T G G A T A A-3' (SEQ. ID. No. 3) or
(III)

5'-G C T A T G T C G A C A C C C A A T T C T G A A A-3' (SEQ. ID. No. 4) or
(IV)

5'-C T G T C T C C G C T T C T T C T T C C T G C C A T A G G A G (SEQ. ID. No. 6) or
(V)

5'-T C G T C G C T G T C T C C G C T T C T T C T T C C T G C C A (SEQ. ID. No. 5) or
(VI)

b) against HSV-1, e.g.

5'-G C G G G G C T C C A T G G G G G T C G-3' (SEQ. ID. No. 7)
(VII)

The pharmaceutials of the present invention are also suitable for treating cancer, for example. For example, are active against targets of this nature have the following base sequences, for example:

a) against c-Ha-ras, e.g.

5'-C A G C T G C A A C C C A G C-3' (SEQ. ID. No. 8)
(VIII)

c) c-myc, e.g.

5'-G G C T G C T G G A G C G G G G C A C A C-3' (SEQ. ID. No. 9)
(IX)

5'-A A C G T T G A G G G G C A T -3' (SEQ. ID. No. 10)
(X)

d) c-myb, e.g.

5'-G T G C C G G G G T C T T C G G G C-3' (SEQ. ID. No. 12)
(XI)

e) c-fos, e.g.

5'-G G A G A A C A T C A T G G T C G A A A G-3' (SEQ. ID. No. 14)

-continued (XII)

5'-C C C G A G A A C A T C A T G G T C G A A G-3' (SEQ. ID. No. 15)
(XIII)

5'-G G G G A A A G C C C G G C A A G G G G-3' (SEQ. ID. No. 16)
(XIV)

f) p120, e.g.

5'-C A C C C G C C T T G G C C T C C C A C-3' (SEQ. ID. No. 17)
(XV)

g) EGF receptor, e.g.

5'-G G G A C T C C G G C G C A G C G C-3' (SEQ. ID. No. 18)
(XVI)

5'-G G C A A A C T T T C T T T T C C T C C-3' (SEQ. ID. No. 19)
(XVII)

h) p53 tumor suppressor, e.g.

5'-G G G A A G G A G G A G G A T G A G G-3' (SEQ. ID. No. 20)
(XVIII)

5'-G G C A G T C A T C C A G C T T C G G A G-3'r (SEQ. ID. No. 21)
(XIX)

The pharmaceuticals of the present invention are also suitable, for example, for treating diseases which are affected by integrins or cell-cell adhesion receptors, for example by VLA-4, VLA-2, ICAM, VCAM or ELAM.

Novel antisense oligonucleotide derivatives which are active against targets of this nature have the following base sequences, for example:

a) VLA-4, e.g.

5'-G C A G T A A G C A T C C A T A T C-3' (SEQ. ID. No. 24) or
(XX)

b) ICAM, e.g.

5'-C C C C C A C C A C T T C C C C T C T C-3' (SEQ. ID. No. 25)
(XXI)

5'-C T C C C C C A C C A C T T C C C C T C-3' (SEQ. ID. No. 26)
(XXII)

5'-G C T G G G A G C C A T A G C G A G G-3' (SEQ. ID. No. 27)
(XXIII)

c) ELAM-1, e.g.

5'-A C T G C T G C C T C T T G T C T C A G G-3' (SEQ. ID. No. 28)
(XXIV)

5'-C A A T C A A T G A C T T C A A G A G T T C-3' (SEQ. ID. No. 29)
(XXV)

The pharmaceuticals of the present invention are also suitable, for example, for preventing restenosis. For example, oligonucleotide sequences may be employed in this context which are directed against targets which are responsible for proliferation or migration. The examples of targets of this nature are:

1) Nuclear transactivating proteins and cyclines, such as, for example, c-myc, c-myb, c-fos, c-fos/jun, cyclines and cdc2 kinase,
2) Mitogens or growth factors, such as, for example, PDGF, bFGF, EGF, HB-EGF and TGF-β.
3) Cellular receptors, such as, for example, bFGF receptor, EGF receptor and PDGF receptor.

Novel oligonucleotides of the formula I which are active against targets of this nature have the following base sequences, for example:

a) c-myb
5'-G T G T C G G G G T C T C C G G G C-3' (SEQ. ID. No. 13)
(XXVI)

b) c-myc
5'-C A C G T T G A G G G G C A T-3' (SEQ. ID. No. 11)
(XXVII)

c) cdc2 kinase
5'-G T C T T C C A T A G T T A C T C A-3' (SEQ. ID. No. 22)
(XXVIII)

d) PCNA (proliferating cell nuclear antigen of rat)
5'-G A T C A G G C G T G C C T C A A A-3' (SEQ. ID. No. 23)
(XXIX)

The pharmaceuticals may, for example, be used in the form of pharmaceutical preparations which can be administered orally, for example in the form of tablets, coated tablets, hard or soft gelatin capsules, solutions, emulsions or suspensions. Enclosure of the pharmaceuticals in liposomes, which, where appropriate, contain additional components such as proteins, also represents a suitable form of administration. They may also be administered rectally, e.g. in the form of suppositories, or parenterally, e.g. in the form of injection solutions. In order to produce pharmaceutical preparations, these compounds can be processed in therapeutically inert organic and inorganic excipients. Examples of excipients of this nature which are suitable for tablets, coated tablets and hard gelatin capsules are lactose, corn starch or derivatives thereof, tallow and stearic acid or salts thereof. Water, polyols, sucrose, invert sugar and glucose are suitable excipients for preparing solutions. Water, alcohols, polyols, glycerol and vegetable oils are suitable excipients for injection solutions. Vegetable and hardened oils, waxes, fats and semiliquid polyols are suitable excipients for suppositories. The pharmaceutical preparations may also contain preservatives, solvents, stabilizers, wetting agents, emulsifiers, sweeteners, colorants, flavorants, salts for altering the osmotic pressure, buffers, coating agents and antioxidants, and also, where appropriate, additional therapeutic active compounds.

Preferred forms of administration are topical administration, local administration, for example using a catheter, and also injections. For an injection, the antisense oligonucleotide derivatives are formulated in a liquid solution, preferably in a physiologically acceptable buffer, such as, for example, Hank's solution or Ringer's solution. However, the antisense oligonucleotides can also be formulated in solid form, and dissolved or suspended prior to use. The dosages which are preferred for systematic administration are from approximately 0.01 mg/kg to approximately 50 mg/kg of body weight and per day.

In a quite general manner, the invention extends to the use of compounds of the formula I as DNA probes or primers in DNA diagnostics, and generally as aids in molecular biology.

EXAMPLES

The compounds (1)–(16), which are mentioned in the examples, have the following structural formulae.

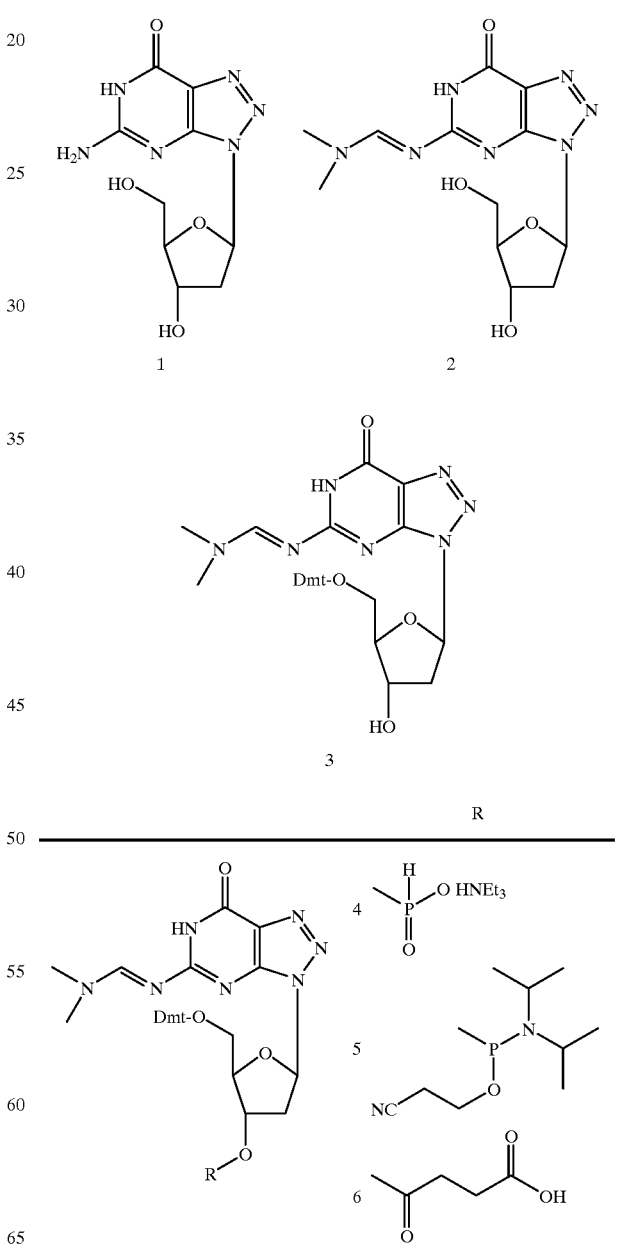

-continued

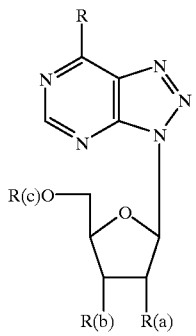

| | R(a) | R(b) | R(c) | R |
|---|---|---|---|---|
| (7) | —COCH$_3$ | —COCH$_3$ | —COCH$_3$ | —NH—CO—C$_5$H$_{19}$ |
| (8) | —COCH$_3$ | —COCH$_3$ | —COCH$_3$ | NH$_2$ |
| (9) | OH | OH | OH | NH$_2$ |
| (10) | OH | OH | OH | —NH—CO—C$_6$H$_5$ |
| (11) | OH | OH | OH | —N=CH—N(CH$_3$)$_2$ |
| (12) | OH | OH | OH | CH$_3$<br>—N=CH—N(CH$_3$)$_2$ |
| (13) | OH | OH | Dmt | " |
| (14) | Tms | OH | Dmt | " |
| (15) | OH | Tms | Dmt | " |
| (16) | Tms | TEP | Dmt | " |

Example 1

5-Amino-3-(2-deoxy-β-D-erythropentofuranosyl)-3H-1,2,3-triazolo [4,5]pyrimidin-7-(6H)-one-5'-O-triphosphate, triethylammonium salt (8-aza-2'-deoxyguanosine 5'-triphosphate)

While warming gently, 3-(2-deoxy-β-D-erythropentofuranosyl)-5-amino-3H-1,2,3-triazole [4,5]pyrimidin-7-(6H)-one (8-aza-2'-deoxyguanosine (1)) (26 mg; 0.09 mmol) was brought, together with 1,8-bis(dimethylamino)-napthalene 33 mg, 0.15 mmol), into solution in tri-methyl phosphate (0.25 ml). After the solution had been cooled down to 0° C., freshly distilled POCl$_3$ (12 μl, 0.13 mmol) was added. The reaction was maintained at 4° C. for 4 h, and a solution composed of tri-n-butylammonium disphosphate (0.5 mM in DMF, 1 ml) and tri-n-butylamine (100 μl, 0.42 mmol) was then added. After this mixture had been stirred at 0° C. for 3 min, 1 M TBC buffer (10 ml) was added and the whole was evaporated to dryness. The residue was chromatrographed on DEAD Sephadex® (1.5×20 cm column, HCO$_3$⁻ form). After the column had been washed with approximately 500 ml of H$_2$O, chromatography took place using a linear gradient of H$_2$O/0.9 M TBC buffer (1 l in each case). This yielded a main zone at approximately 0.5 M TBC buffer (0.019 mM, 20 %). TLC (silica gel, i-propanol/H$_2$O/NH$_3$, 3:1:1): R$_f$ 0.2. UV (H$_2$O): λ$_{max}$ 256 nm. $^{31}$P-NMR (0.1 M Tris-HCl, pH 8.0, 100 mM EDTA/D$_2$O): −10.27 (d,J=19.3, P$_x$); −10.63 (td, J=20.2 and 6.0, P$_α$); −22.60 (t, J=19.8, P$_β$).

Example 2

3-(2-Deoxy-β-D-erythropentofuranosyl)-5-{[(dimentyl-amino)methylidene]amino}-3H-1,2,3-triazolo [4,5-d]-pyrimidin-7-(6H)-one (2).

3-(2-Deoxy-β-D-erythropentofuranosyl)-5-amino-3H-1,2,3-triazolo [4,5-d]pyrimidin-7-(6H)-one (8-aza-2'-deoxyguanosine (1)) (290 mg; 1.06 mmol) was dissolved in abs. DMF (7 ml), and N,N-dimethylformamide diethyl acetal (5 ml) was added. After the mixture had been stirred at room temperature for 24 hours, it was subjected to rotary evaporation in vacuo, and the residue was coevaporated with toluene. The residue was purified by means of chromatography on silica gel (column: 20×4 cm 0.5 bar, CH$_2$Cl$_2$/MeOH 8:2). Compound (2) (320 mg, 92%) was obtained as a colorless foam which crystallized from MeOH. M.p. 236° C. TLC (CH$_2$Cl$_2$/MeOH 8:2): R$_f$ 0.7. UV (MeOH): 301 (26500), 244 (15500).

$^1$H-NMR ((D$_6$)DMSO: 8.66 (s, CH); 6.43 (t, J=6.32, H-C(1')); 5.40 (br.s, OH-C(3')); 4.79 (br.s, OH-C(5')); 4.48 (m, H-C(3')); 3.85 (m, H-C(4')); 3.57 (m, H-C(5')); 3.19, 3.06 (2 s, 2CH$_3$); 2.90 (m, H$_β$-C(2')); 2.34 (m, H$_{(α)-C}$(2')).

C$_{12}$H$_{17}$N$_7$O$_4$ (323.31) calculated C 44.56, H 5.29, N 30.32 found C 44.64, H 5.26, n 30.37.

Example 3

3-[2-Deoxy-5-O-(4,4'-dimethoxytrityl-β-D-erythropentofuranosyl]-5-{[(dimethylamino)methylidene]amino}-3 H-1,2,3-triazolo[4,5-d]pyrimidin-7-(6H)-one (3).

The amino-protected 8-aza-2'-deoxyguanosine (2) from Example 2 (170 mg, 0.53 mmol) was treated by being repeatedly coevaporated with abs. pyridine and then taken up in 6 ml of the latter. 4,4'-Dimethoxytrityl chloride (260 mg, 0.7 mmol) was added at room temperature, and this mixture was stirred for 3 hours. The solution was then poured into 5% NaHCO$_3$ (40 ml), and this mixture was extracted twice with 30 ml of CH$_2$Cl$_2$ on each occasion. The combined organic phases were dried over Na$_2$SO$_4$ and subjected to rotary evaporation in vacuo. The residue was chromatographed on silica gel (column: 15×4 cm, 0.5 bar, CH$_2$Cl$_2$/MeOH 95:5). 270 mg (82%) of a colorless foam were obtained. TLC (CH$_2$Cl$_2$/MeOH 95:5) R$_f$ 0.3. UV (MeOH): 302 (24600), 235 (35000).

$^1$H-NMR ((D$_6$)DMSO): 12.03 (s, NH); 8.66 (s, CH); 7.39–6.70 (2 m, aromat. H); 6.48 (m, H-C(1')); 4.57 (m, H-C(3')); 3.97 (m, H-C(4')); 3.69 (s, 2OCH$_3$); 3.37 (m, H-C(5')), 3.22, 3.07 (2s, 2CH$_3$); 2.90 (m, H$_β$-C(2')); 2.40 (m, H$_{(α)}$-C(2')).

C$_{33}$H$_{35}$N$_7$O$_6$ (625.68) calculated C 63.34, H 5.64, N 15.67 found C 63.42, H 5.72, N 15.71

Example 4

3-[2-Deoxy-5-O(4,4'-dimethoxytrityl)-β-D-erythropentofuranosyl]-5-{[(dimethylamino)methylidene]amino}-3H-1,2,3-triazolo[4,5-d]pyrimidin-7-(6H)-one 3'(triethylammonium phosphonate) (4).

1,2,4-Triazole (0.54 g, 7.56 mmol) was added to a solution of PCl$_3$ (200 μl, 0.22 mmol) and N-methylmorpholine (2.7 ml, 2.24 mmol) in CH$_2$Cl$_2$ (10 ml). The solution was left to stir for 30 min and then cooled down to 0° C. The 5'-O-dimethoxytrityl compound 3 from Example 3 (220 mg, 0.35 mmol) was dried by coevaporation with dried MeCN and was then added after being dissolved in CH$_2$Cl$_2$ (5 ml). After it had been stirred for 10 min, the mixture was poured into 1 M (Et$_3$NH)HCO$_3$ (TBC buffer, pH 8.0, 30 ml), and this latter mixture was extracted twice by shaking with CH$_2$Cl$_2$ and separating the phases. The combined organic solutions were dried over Na$_2$SO$_4$ and evaporated. The residue was chromatographed on silica gel (column: 4×15 cm, 0.5 bar; 1. CH$_2$Cl$_2$/Et$_3$N 98:2, 2. CH$_2$Cl$_2$/MeOH/Et$_3$N 88:10:2). The substance present in the main zone was taken up in CH$_2$Cl$_2$ (10 ml), and this solution was extracted several times by shaking with 0.1 M TBC buffer as a colorless foam. TLC (CH$_2$Cl$_2$/MeOH/Et$_3$N 88:10:2): R$_f$ 0.3. UV (MeOH): 285 (sh, 14900), 303 (18400).

$^1$H-NMR ((D$_6$)DMSO): 11.68 (s, NH); 8.83 (s, CH); 7.77, 5.45, (d, J=585, HP); 7.24–6.69 (2 m, aromat. H); 6.53 (m, J=4.5, H-C1')); 5.22 (m, H-C(3')); 4.09 (m, H-C(4')); 3.67 (s, 2 OCH$_3$); 3.07, 3.23 (s, 2 CH$_3$, H-C(5')); 2.97 (m, CH$_3$CH$_2$); 2.56 (m, H-C(2')); 1.13 (m, CH$_3$CH$_2$).

$^{31}$P-NMR ((D$_6$)DMSO): 1.16 ($^1$J(P,H)=585); $^3$J(P,H-C(3')=8.90.

C$_{39}$H$_{51}$N$_8$O$_8$P$_1$ (790.87) calculated C 59.23, H 6.49, N 14.17 found C 59.33, H 6.79, N 13.95

Example 5

3-[2-Deoxy-5'-O-(4,4'-dimethoxytrityl)-β-D-erythropentofuranosyl]-5-{[(dimethylamino)methylidene]amino}-3H-1,2,3-triazolo[4,5-d]pyrimidin-7-(6H)-one 3'-[(2-cyanoethyl)-N,N-diisopropylphosphoramidite] (5).

(i-Pr)$_2$EtN (56 μl, 0.27 mmol) and chloro(2-cyanoethoxy)-diisopropylaminophosphane (115 μl, 0.51 mmol) were added to a solution of compound (3) from Example 3 (50 mg, 0.08 mmol) in CH$_2$Cl$_2$ (1 ml). The mixture was stirred at room temperature for 2 hours under argon. It was then poured into 5% NaHCO$_3$ (3 ml), and this mixture was extracted twice with CH$_2$Cl$_2$ (30 ml). The combined organic phases were dried over Na$_2$SO$_4$ and evaporated to dryness on a rotary evaporator. The residue was chromatographed on silica gel (column: 7×2 cm, 0.5 bar, CH$_2$Cl$_2$/AcOEt/Et$_3$N 45:45:10). It was possible to distinguish two overlapping zones of diastereomers of the phosphoramidite (5), which diastereomers were obtained as a coloroless foam (35 mg, 55%). TLC (CH$_2$Cl$_2$/AcOET/Et$_3$N 45:45:10): R$_f$ 0.4.

$^{31}$P-NMR ((D$_6$)DMSO): 149.4, 148.9.

Example 6

2-[2-Deoxy-5-O-(4,4-dimethoxytrityl)-3'-O-succinyl-β-D-erythropentofuranosyl]-5-{[(dimethylamino)methylidene]amino}-3H-1,2,3-triazolo[4,5-d]pyrimidin-7-(6H)-one (6).

4-Dimethylaminopyridine (30 mg, 0.23 mmol) and succinic anhydride (90 mg, 0.88 mmol) were added to a solution of the protected nucleoside (3) from Example 3 (110 mg, 0.18 mmol) in pyridine (5 ml). The mixture was left to stir at room temperature for 48 hours. The reaction was stopped by adding 2 ml of water. After the mixture had been evaporated to dryness, the residue was coevaporated with toluene in order to remove any remaining pyridine. The residue was dissolved in a little CH$_2$Cl$_2$, and this solution was washed with a 10% aqueous solution of citric acid and with water. The organic phase was dried over Na$_2$SO$_4$ and concentrated in vacuo. After the residue had been dissolved in CH$_2$Cl$_2$/pyridine (95:5, 2 ml), n-pentane/ether (1:1, 30 ml) was added rapidly. The supernatant was filtered off and a colorless powder remained (85 mg, 66%). TLC (CH$_2$Cl$_2$/MeOH 9:1): R$_f$ 0.25.

$^1$H-NMR ((D$_6$)DMSO): 8.71 (s, CH); 7.28–6.75 (2 m, aromat. H); 6.46 (m, J=4.1, H-C(1')); 5.48 (m, H-C(3')); 4.21 (m, H-C(4')); 3.36 (s, 2 OCH$_3$); 3.18, 3.05 (2 s, 2 CH$_3$); 3.10 (m, H-C(5')); 2.51 (m, H-C(2'), 2 CH$_2$).

Example 7

7-(Benzoylamino)-1,2,3-triazolo[4,5-d]pyrimidine

8-Azaadenine (200 mg, 1.47 mmol) is evaporated three times in dry pyridine and then taken up in 5 ml of dry pyridine. Benzoyl chloride (0.28 ml, 2.20 mmol) is then added dropwise, and the mixture is stirred at 60° C. for 3 hours. It is then boiled under reflux for a further hour. The reaction mixture is left to stand overnight and is then concentrated down to approximately 1 ml. 15 ml of cold water are added to this mixture, which is left to stir for 5 min; the resulting precipitate is filtered off with suction. The faintly yellowish precipitate is washed twice in each case with 1 ml of cold water and 1 ml of cold acetonitrile. 0.30 g (85%) of colorless crystals are obtained (MeOH). M.p.= 263° C. (decomposition). TLC (silica gel, CH$_2$Cl$_2$/MeOH= 8:2); R$_f$=0.6. UV (methanol) λ$_{max}$ (ε)=242 (12100); 291 (16000).

$^1$H-NMR (D$_6$-DMSO) δ: 7.58; 7.69; 8.13 (arom. -H$_5$) 8.89 (s, H-5), 11.99 (s-N$^6$-H).

C$_{11}$H$_8$N$_6$O calculated C 54.99 H 3.36 N 34.99. found C 55.10 H 3.34 N 35.04.

Example 8

7-(Nonanoylamino)-3-[(2,3,5-tri-O-acetyl)-β-D-ribofuranosyl]-3H-1,2,3-triazolo[4,5-d]pyrimidine (7)

500 mg (1.81 mmol) of 7-nonanoylamido-1,2,3-triazolo [4,5-d]pyrimidine are evaporated to dryness three times in dry pyridine. The residue is taken up in 20 ml of dry acetonitrile. 0.58 g (1.81 mmol) of 1,2,3,5-tetra-O-acetyl-β-D-ribofuranose is added, 0.64 ml (5.43 mmol) of tin tetrachloride is added dropwise, and the reaction mixture is stirred at room temperature for 24 hours. The reaction solution is then added to 25 ml of a saturated solution of sodium hydrogen carbonate, and this mixture is extracted four times with 15 ml of dichloromethane on each occasion. After having been dried over sodium sulfate, the combined organic phases are evaporated to dryness. 0.81 g of an oily residue is obtained. The product mixture is fractionated by column chromatography (5.5×30 cm column, silica gel, eluent: CH$_2$Cl$_2$/MeOH 95:5). 0.27 g (28%) of a colorless nucleoside is obtained from the more rapidly migrating zone. TLC (silica gel, CH$_2$Cl$_2$/MeOH): R$_f$=0.75. UV (methanol) λ$_{max}$ (ε)=275 (16800).

$^1$H-NMR (D$_6$-DMSO) δ: 0.82 (m, —CH$_3$-9"); 1.22 (m, —(CH$_2$)$_5$—); 1.62 (m, J=6.8 Hz, —CH$_2$-3"); 1.93; 2.08; 2.11 (3s, O=CCH$_3$); 2.61 (t, J=7.2 Hz, —CH$_2$-2"); 4.26 (m, H-5'); 4.52 (m, H-4'); 5.77 (m, H-3'); 6.12 (m, H-2'); 6.63 (d, J=3.4 Hz, H-1'); 8.89 (s, H-5); 11.48 (s, br, N$^6$-H).

Example 9

Glycosylation of 7-amino-1,2,3-triazolo[4,5-d]pyrimidine with 1,2,3,5-tetra-O-acetyl-β-D-ribofuranose.

340 mg (2.5 mmol) of 7-amino-1,2,3-triazolo[4,5-d] pyrimidine and 800 mg (2.5 mmol) of 1,2,3,5-tetra-O-acetyl-β-D-ribofuranose are suspended in 10 ml of dry acetonitrile. 0.88 ml (7.5 mmol) of tin tetrachloride is added dropwise, under argon, to this mixture within the space of 5 min, and the whole is then stirred at room temperature for 24 hours. The resulting solution is poured carefully onto 32 ml of a saturated solution of NaHCO$_3$. The precipitate which arises is filtered off with suction and washed twice with 10 ml of water on each occasion. The filtrate and the washing water are extracted four times with 15 ml of methylene chloride on each occasion. After drying over Na$_2$SO$_4$, and stripping off the solvent, 0.87 g of a faintly yellowish foam is obtained. The reaction products are fractionated by column chromatography (column: 5.5×20 cm, silica gel, CH$_2$Cl$_2$/MeOH 98:2–90:10).

Example 10

7-Amino-3-[(2,3,5-tri-O-acetyl)-β-D-ribofuranosyl]-3H-1, 2,3-triazolo[4,5-d]pyrimidine (8)

The more rapidly migrating zone yields 0.34 g (34%) of a colorless foam. TLC (silica gel, CH$_2$Cl$_2$/MeOH 9:1): R$_f$=0.45 UV (methanol) λ$_{max}$ (ε)=280 (10900).

$^1$H-NMR (D$_6$-DMSO) δ: 1.89; 2.10; 2.11 (3s, 2',3',5'—O—C=O); 4.20 (m, H$_2$-5'); 4.48 (m, H-4'); 5.74 (t, J=5.5 Hz, H-3'); 6.07 (t, J=3.7 Hz, H-2'): 6.48 (d, J=2.8 H-1'); 8.25; 8.6 (2s, N$^6$-H$_2$), 8.34 (s, H-5).

C$_{15}$H$_{18}$N$_6$O$_7$ calculated C 45.68 H 4.61 N 21.31 found C 45.98 H 4.72 N 21.40.

Example 11
7-Amino-2-[(2,3,5-tri-O-acetyl)-β-D-ribofuranosyl]-2H-1,2,3-triazolo[4,5-d]pyrimidine 0.46 g (47% of a colorless foam are obtained from the more slowly migrating zone of the chromatographic purification step. TLC (silica gel, $CH_2Cl_2$/MeOH): $R_f$=0.35 UV (methanol) $\lambda_{max}$ (ε)=253 (3900), 300 (10400).

$^1$H-NMR ($D_6$-DMSO) δ: 1.94; 2.07; 2.11 (3s, 2',3',5'—O—C=O); 4.25 (m, $H_2$-5'); 4.52 (m, H-4'); 5.74 (t, J=6.0, H-3'); 5.91 (d, J=3.4, H-2'); 6.53 (s, H-1'); 8.3; 8.45 (2s, $N^6$-$H_2$); 8.34 (H-5).

$C_{15}H_{18}N_6O_7$ calculated C 45.68 H 4.61 N 21.31 found C 45.86 H 4.71 N 21.22

Example 12
7-Amino-3(β-D-ribofuranosyl)-3H-1,2,3-triazolo[4,5-d]pyrimidine (8-azaadenosine, 9)

2.04 g (5.17 mmol) of compound (8) are stirred, at room temperature for 2 hours, in 5 ml of methanol and 5 ml of aqueous ammonia (25%). After evaporation to dryness and recrystallization of the residue in 3 ml of water, 1.04 g (75%) of colorless crystals are obtained which decompose at 217° C. TLC (silica gel, $CH_2Cl_2$/MeOH=8:2): $R_f$=0.45. UV: $\lambda_{max}$ (pH 7)=279 (11600); $\lambda_{max}$ (pH 1)=263, $\lambda_{max}$ (pH 14)=279.

$^1$H-NMR ($D_6$-DMSO) δ: 3.56 (m, $H_2$-5'); 4.01 (m, H-4'), 4.29 (m, 3'); 4.85 (m, H-2'); 5.01 (t, J=5.9 Hz, HO-5'); 5.28 (d, J=5.7, HO-3'); 5.56 (d, J=6.0 HO-2'); 6.15 (d, J=5.2 Hz, H-1'); 8.31 (s, H-5); 8.53; 8.19 (2s, $N^7H_2$).

Example 13
7-Amino-2-(β-D-ribofuranosyl)-2H-1,2,3-triazolo[4,5-d]pyrimidine 0.81 g (2.05 mmol) of the compound from Example 11 is stirred, at room temperature for 2 hours, in 5 ml of methanol and 5 ml of aqueous ammonia (25%). After evaporation to dryness and recrystallization of the residue in 2.5 ml of water, 0.32 g (59%) of colorless crystals is obtained, which crystals decompose at 209° C. TLC ($CH_2Cl_2$/MeOH=8:2): $R_f$=0.20 UV (methanol) $\lambda_{max}$ (ε)=255 (4400), 263 (4100), 297 (10400).

$^1$H-NMR ($D_6$-DMSO) δ: 3.59 (m, $H_2$-5'); 4.06 (m, H-4'); 4.33 (m, H-3'); 4.61 (m, H-2'); 4.76 (t, J=5.3 Hz, HO-5'); 5.27 (d, J=5.8 Hz, HO-3'); 5.68 (d, J=5.5 Hz, HO-2'); 6.08 (s, J=3.4 Hz, H-1'); 8.31 (s, H-5); 8.12 (s, $N^7H_2$).

Example 14
7-Benzoylamino-3-(β-D-ribofuranosyl)-3H-1,2,3-triazolo[4,5-d]pyrimidine (10).

100 mg (0.37 mmol) of 7-amino-3-β-D-ribofuranosyl-3H-1,2,3-triazolo[4,5-d]pyrimidine are initially introduced in 5 ml of dry pyridine. 0.47 ml (3.7 mmol) of trimethylsilyl chloride is added dropwise to this solution under an argon atmosphere. After the mixture has been stirred at room temperature for half an hour (monitoring by TLC), 0.25 ml (2.0 mmol) of benzoyl chloride is added dropwise, and this reaction mixture is stirred at room temperature for 4 hours. It is then cooled down to 0–5° C. and 1 ml of water is added followed, 5 min later, by 2 ml of aqueous ammonia (25%); this mixture is then stirred for a further 30 min. The solvent is stripped off and the residue is then evaporated with toluene. The residue is taken up in 15 ml of a saturated solution of $NaHCO_3$, and this mixture is extracted one with 25 ml of methylene chloride and several times with ethyl acetate. The combined organic phases are dried using $Na_2SO_4$.

After the solvent has been stripped off, 0.05 g (36%) is obtained of a colorless, crystalline substance which, after crystallization from methanol, melts with decomposition at 188° C. TLC (silica gel, $CH_2Cl_2$/MeOH=9:1): $R_f$=0.25 UV (methanol) $\lambda_{max}$ (ε)=242 (9400), 282 (20300).

$^1$H-NMR ($D_6$-DMSO) δ: 3.56 (m, $H_2$-5'); 4.04 (m, H-4'); 4.36 (m, H-3'); 4.84 (t, HO-5'); 4.92 (m, H-2'); 5.33 (d, J=5.2 Hz, HO-3'); 5.66 (d, J=5.4 Hz, HO-2'); 6.30 (d, J=4.3 Hz, 1'); 7.54–8.11 (m, arom.-$H_5$); 8.94 (s, H-5); 11.99 (s, br, $N^6$-H).

$C_{16}H_{16}N_6O_6$ calculated C 51.60 H 4.34 N 22.57. found C 51.49 H 4.43 N 22.74.

Example 15
7-{[(Dimethylamino)methylidene]amino}-3-(β-D-ribofuranosyl)-3H-1,2,3-triazolo[4,5-d]pyrimidine (11).

100 mg (0.37 mmol) of 7-amino-3-β-D-ribofuranosyl-(3H)-1,2,3-triazolo[4,5-d]pyrimidine are left to stir overnight, at room temperature, in 2 ml of dry DMF and 0.25 ml (1.85 mmol) of N,N-dimethylformamide dimethyl acetal. 4 ml of methanol is then added to this reaction mixture. After having been stirred for a further 2 hours, the mixture is evaporated to dryness, and the residue is coevaporated with toluene and then chromatographed on silica gel. (Column: 3×20 cm, eluent $CH_2Cl_2$/MeOH 98:2–90:10). 0.06 g (52%) of a colorless, glassy solidified substance is obtained in the main zone. TLC (silica gel, $CH_2Cl_2$/MeOH=9:1): $R_f$=0.25 UV $\lambda_{max}$ (ε)=235, 325.

$^1$H-NMR ($D_6$-DMSO) δ: 3.21; 3.27 (2s, N $(CH_3)_2$); 3.55 (m, $H_2$-5'), 4.00 (m, H-4'); 4.31 (m, H-3'); 4.87 (m, H-2'); 4.96 (t, HO-5'); 5.32 (d, HO-3'); 5.60 (d, HO-2'); 6.19 (d, J=4.7 Hz, H-1'); 8.57 (s, H-5); 9.06 (s, N=CH).

Example 16
7-{[1-(Dimethylamino)ethylidene]amino}-3-(β-D-ribofuranosyl)-3H-1,2,3-triazolo[4,5-d]pyrimidine (12).

0.91 ml (5.59 mmol) of N,N-dimethylacetamide dimethyl acetal is added to 500 mg (1.86 mmol) of 9 in 10 ml of analytical grade methanol. The suspension is left to stir at room temperature for 14 hours. The solution which results is freed from the solvent on a rotary evaporator, and the residue is coevaporated with toluene. A further 10 ml of methanol are added to the residue, and this mixture is stirred at room temperature for 2 hours. After the solvent has been separated off, the residue is chromatographed on silica gel (column, 4×20 cm, eluent $CH_2Cl_2$/MeOH=98:2–90:10). Yield: 0.48 g (76%) of a colorless foam. TLC (silica gel, $CH_2Cl_2$/MeOH= 9:1): $R_f$=0.35 UV (methanol) $\lambda_{max}$ (ε)=233 (9300), 270 (3600), 324 (26100).

$^1$H-NMR ($D_6$-DMSO) δ: 2.28 (s, N=C—$CH_3$); 3.20 (s, N$(CH_3)_2$); 3.55 (m, $H_2$-5'); 4.00 (m, H-4'); 4.30 (m, H-3'); 4.86 (m, H-2'); 4.98 (t, HO-5'); 5.29 (d, J=5.2 Hz, HO-3'); 5.57 (d, J=5.9 Hz, HO-2'), 6.18 (d, J=5.2 hZ, H-1'); 8.54 (S, H-5).

$C_{13}H_{19}N_7O_4$ calculated C 46.28 H 5.69 N 29.07. found C 46.45 H 5.63 N 28.97.

Example 17
7-{[1-(Dimethylamino)ethylidene]amino}-3-[5-O-(4,4'-dimethoxytriphenylmethyl)-β-D-ribofuranosyl]-3H-1,2,3-triazolo[4,5-d]pyrimidine (13).

In order to dry it, 0.34 g (1.00 mmol) of 12 is evaporated twice in dry pyridine. The substance is dissolved in 4 ml of dry pyridine, and 0.41 g (1.20 mmol) of 4,4'-dimethoxytrityl chloride is added; the mixture is then stirred at 40° C. for 2 hours. After the mixture has been cooled down to room temperature, 5 ml of analytical grade methanol are added, and this mixture is stirred for a further 30 minutes. The reaction solution is concentrated down to approximately half its volume. 8 ml of a saturated solution of sodium hydrogen carbonate are then added, and the whole is extracted four times with 10 ml of methylene chloride on each occasion.

The combined organic phases are extracted by shaking with 15 ml of a saturated solution of sodium chloride, dried over sodium sulfate and evaporated. The residue (0.73 g of a pale yellow foam) is further purified using column chromatography (column: 2×20 cm, silica gel, $CH_2Cl_2$/MeOH 95:5). Yield: 0.52 g (81% of a colorless foam. TLC (silica gel, $CH_2Cl_2$/MeOH=9:1): $R_f$=0.45 UV (methanol) $\lambda_{max}$ ($\epsilon$)=234 (29900), 275 (13800), 324 (24800).

$^1$H-NMR ($D_6$-DMSO) δ: 2.24 (s, N=$CCH_3$); 3.10 (m, $H_2$-5'); 3.19 (s, N($CH_3$)$_2$); 3.69 (s, ($OCH_3$)$_2$); 4.14 (m, H-4'); 4.51 (m, H-3'); 4.86 (m, H-2'); 5.28 (d, J=6.2 Hz, HO-3'); 5.68 (d, J=5.1 Hz, HO-2'); 6.25 (d, H-1'); 6.71–7.26 (m, 13 arom. H); 8.54 (s, H-5).

$C_{34}H_{37}N_7O_6$ calculated C 63.83 H 5.84 N 15.33. found C 63.64 H 5.84 N 15.31.

Example 18

7-{[1-(Dimethylamino)ethylidene]amino}-3-{5-O-(4,4'-dimethoxytriphenylmethyl)-2-O-[tris(1-methylethyl)silyl]-β-D-ribofuranosyl}-3H-1,2,3-triazolo[4,5-d]pyrimidine (14)

0.35 g (0.55 mmol) of the dried trityl compound 13 is initially introduced in 4 ml of dry pyridine. 140 mg (0.82 mmol) of silver nitrate are added to this solution, after which 145 μl (0.69 mmol) of triisopropyl chloride, which has previously been dissolved in 5 ml of tetrahydrofuran, are added under argon. The mixture is left to stir at room temperature with light being excluded. After 24 hours, a further 120 μl (0.55 mmol) of triisopropyl-silyl chloride are added, and the mixture is left to stir at room temperature for a further 48 hours. The silver chloride which has precipitated out is filtered off and washed with a little tetrahydrofuran; 10 ml of a saturated solution of sodium hydrogen carbonate are then added to the filtrate. This is extracted four times with 10 ml of dichloromethane on each occasion, and the combined organic phases are dried over sodium sulfate. Following evaporation to dryness, 0.60 g is obtained of a faintly yellowish oil. The reaction products are purified and fractionated by means of column chromatography. (Column, 3×20 cm, silica gel, eluent ethyl acetate/petroleum ether 8:2). 0.31 g (71%) of a colorless foam are obtained from the more rapidly migrating main zone.

TLC (silica gel, ethyl acetate/petroleum ether 9:1): $R_f$=0.30.

UV (methanol) $\lambda_{max}$ ($\epsilon$)=234 (29600), 274 (6800), 325 (25900).

$^1$H—NMR ($D_6$—DMSO) δ: 0.83–0.97 (m, Si—[CH ($CH_3$)$_2$]; 2.24 (s, N=$CCH_3$), 3.10 (m, $H_2$-5'); 3.19 (s, N($CH_3$)$_2$); 3.70 (s, (O—$CH_3$)$_2$); 4.19 (m, H-4'); 4.43 (m, H-3'); 5.21 (t, J=4.4 Hz, H-2'); 5.27 (d, J=6.3 Hz, HO-3'); 6.30 (d, J=4.3 Hz, H-1'); 6.75–7.35 (m, 13 arom. H); 8.53 (s, H-5).

$C_{43}H_{57}N_7O_6$—Calculated: C, 64.87; H, 7.23; N,12.23. Found: C, 64.94; H, 7.37; N, 12.13.

Example 19

7-{[1-(Dimethylamino)ethylidene]amino}-3-{5-O-(4,4'-dimethoxytriphenylmethyl)-3-O-[tris(1-methylethyl)silyl]-β-D-ribofuranosyl}-3H-1,2,3-triazolo[4,5-d]pyrimidine (15)

0.08 g (18%) of a colorless foam are obtained from the more slowly migrating zone of the column chromatography which was carried out as described above for compound 14.

TLC (silica gel), ethyl acetate/petroleum ether 9:1): $R_f$=0.15.

UV (methanol) $\lambda_{max}$ ($\epsilon$)=234 (29800), 274 (7400), 327 (24700).

$^1$H—NMR ($D_6$—DMSO) δ: 0.98 (s, Si[CH($CH_3$)$_2$]$_3$); 2.19 (s, N=$CCH_3$); 3.10 (m, $H_2$-5'); 3.18 (s, N($CH_3$)$_2$); 3.68 (s, ($OCH_3$)$_2$); 4.17 (m, H-4'); 4.92 (m, H-3', H-2'); 5.64 (d, J=5.1 Hz, HO-2'); 6.27 (d, J=6.0 Hz, H-1'); 6.70–7.20 (m, 13 arom. H); 8.55 (s, H-5).

Example 20

7-{[1-(Dimethylamino)ethylidene]amino}-3-{5-O-(4,4'-dimethoxytriphenylmethyl)-2-O-[tris(1-methylethyl)silyl]-β-D-ribofuranosyl}-3H-1,2,3-triazolo[4,5-d]pyrimidine-3-O-phosphonate, triethylammonium salt (16)

0.67 g (9.75 mmol) of 1,2,4-triazole is added, under an argon atmosphere, to a solution of 114 μl (1.3 mmol) of phosphorus trichloride and 1.43 ml (13.0 mmol) of N-methylmorpholine in 10 ml of dry dichloromethane. After the reaction mixture has been stirred at room temperature for 30 min, it is cooled down to 0° C. and the silyl compound (14), dissolved in 2.5 ml of dry dichloromethane, is added dropwise within the space of 10 min. The reaction mixture is stirred at 0° C. for a further 20 min and then hydrolysed with 1 M TBC buffer. The aqueous phase is extracted three times with 20 ml of dichloromethane on each occasion. The combined organic phases are dried over sodium sulfate and evaporated to dryness. The residue is chromatographed on a silica gel column (3×10 cm, $CH_2Cl_2$/MeOH/TEA 88:10:2). The fractions containing the product are together concentrated by evaporation, and the residue is taken up in 20 ml of dichloromethane; this solution is extracted by shaking four times with 5 ml of 0.1 M TBC buffer on each occasion, dried over sodium sulfate and freed from the solvent. Yield: 0.21 g (83%) of a colorless foam.

TLC (silica gel, $CH_2Cl_2$/MeOH/TEA 88:10:2): $R_f$=0.6.

UV (methanol) $\lambda_{max}$ ($\epsilon$)=234 (27300), 274 (11700), 325 (16400).

$^1$H—NMR ($D_6$—DMSO) δ: 0.75–0.95 (m, Si[CH($CH_3$)$_2$]$_3$); 1.15; 2.99 (m, ($CH_3CH_2$)$_3$N); 2.24 (s, N=$CCH_3$); 3.20 (s, N($CH_3$)$_2$); ($H_2$-5' verdeckt); 3.69 (s, (O—$CH_3$)$_2$); 4.40 (m, H-4'); 4.79 (m, H-3'); 5.44 (m, H-2'); 5.50 u. 7.91 (d, $^1$J=602 Hz, P—H); 6.27 (d, J=6.0 Hz, H-1'); 6.76–7.40 (m, 13 arom. H); 8.50 (s, H-5); 10.90 (s, br, $N^+$—H). $^{31}$P—NMR δ: 2.55 (dd, $^1P_{PH}$=602 $H_2$, $^3J_{PH}$=9.5 $H_2$).

Example 21

Solid-phase Synthesis of the Oligoribonucleotides Using the Phosphonate Method

The oligoribonucleotides are synthesized on a 1 μmol scale using the phosphonate technique and employing an Applied Biosystems, Weiterstadt, DNA synthesizer. Final oxidation is carried out manually.

1. The oligoribonucleotides are cleaved off from the CPG support, on the support column, by means of a 16-hour exposure to the action of ammonia (25% aqueous solution/ethanol 3:11).

2. Elimination of the Base Protective Groups

The ammoniacal solution of the oligomers is heated in a water bath at 55° C. for 16 hours in the case of the unmodified (AU)$_6$ sequence, and at 40° C. for 3 hours in the case of the dodecamers containing 8-azaadenosine. The solutions are evaporated to dryness at room temperature, and the residues are coevaporated with abs. ethanol.

3. The 2'-silyl protective groups were eliminated by a 16-hour exposure, at room temperature, to the action of a one-molar solution of TBAF/THF.

Example 22

Synthesis of 5'-($z^8$A-U)$_6$-3' (17)

The 3'-phosphonate of 8-azaadenosine is employed for synthesizing the oligoribonucleotide 5'-($z^8$A-U)$_6$-3' (17). Here, compound (16) is employed together with 5'-MeO)$_2$Tr-, 2'-t-BuMe$_2$Si-protected 3'-phosphonates of uridine.

The oligonucleotides are synthesized on Controlled Pore Glass (CPG) in the 3' to 5' direction, with the 3'-terminally protected nucleoside being bound covalently to the solid phase via a succinyl spacer. At the beginning of the synthesis, the 5'Dmt group of the support-bound nucleoside is eliminated using 2.5% dichloroacetic acid in dichloromethane. Coupling then takes place with the phosphonate which has been activated with pivaloyl chloride. In order to avoid incorrect sequences, unreacted 5'-OH groups are reacted with isopropyl phosphite.

Example 23
Purification of the Oligoribonucleotides

1.) Preliminary Desalting

Using Qiagen tip 500 anion exchange columns. A ®Qiagen column is equilibrated with 5 ml of 0.1 M TBC buffer, loaded with the oligomer solution and washed with 5 ml of 0.1 M TBC buffer. After that, the oligomers are eluted from the column with 1 M TBC buffer. The product fractions are detected using UV/TLC plates. The buffer solutions are removed from the oligomer-containing fractions using a ®Speed Vac centrifuge under vacuum.

2.) Preparative HPLC

The oligomers were isolated by reverse phase HPLC on a RP 18 ®LiChrosorb column. For this purpose, the oligomer is taken up in 400 $\mu$l of a 1% aqueous solution of diethyl pyrocarbonate (DEPC), and this sample is then heated at 95° C. for 2–3 min, and then cooled rapidly to 0° C., in order to prevent the formation of secondary structures. DEPC is an RNase inhibitor. A sample (10 $\mu$l) of this solution is then injected in order to determine the retention times. The solution is then added to the RP-18 column in portions of 50–100 $\mu$l; the main peak is then separated off, and the combined fractions are concentrated down to a volume of approximately 5 ml.

Mobile phases:
A: 0.1 M TEAA (sterile, pH 7.5)/CH$_3$CN 95:5
B: CH$_3$CN
System I: 20 min, 0–20% B in A
System II: 30 min, 0–20% B in A
Retention time of oligomer 17

| Oligomer | Retention time [min] | System |
|---|---|---|
| (z$^8$A-U)$_6$ | 28.6 | II |

Flow rate: 1 ml/min

3. Desalting

The 5 ml of oligomer solution are added to the column (Millipore, Eschborn) which has previously been autoclaved and equilibrated with 5 ml of CH$_3$CN, 5 ml of 0.05 M TEAA buffer (pH 7.0)/CH$_3$CN 1:1, and with 5 ml of 0.05 M TEAA buffer; the column is then washed with 5 ml of 0.05 M TEAA solution, and the oligoribonucleotides are eluted from the column using a mixture of MeOH/CH$_3$CN/H$_2$O 1:1:1 in portions of 1 ml. The oligomer-containing fractions are identified by HPLC. After having been lyophilized on a ®Speed Vac concentrator, the oligoribonucleotides are stored at −25° C.

Example 24
Total Hydrolysis of the Oligoribonucleotides 0.2 A$_{260}$ units of the oligomers are dissolved in 200 $\mu$l of tris-HCl buffer (pH 8.3), after which 4 $\mu$g (2 $\mu$l) of snake venom phosphodiesterase (Boehringer Mannheim) are added and the mixture is incubated at 37° C. for 30 min. Following the addition of 3 $\mu$g (5 $\mu$l) of alkaline phosphatase, the solution is maintained at 37° C. for a further 15 min. The nucleoside composition of the reaction solution is then determined by means of HPLC (RP-18 column; mobile phase: 0.1 M TEAA buffer/CH$_3$CN 95:5, flow rate 1 ml/min).

Retention times of the nucleosides:
A=11.4 min z$^8$A=10.0 min 1=4.8 min U=3.6 min
The HPLC peak areas are divided by the respective extinction coefficients and then related to each other.
Extinction coefficients at 260 nm:
$\epsilon$ (A)=15300, $\epsilon$ (z$^8$A)=7100, $\epsilon$ (U)=10200, $\epsilon$ (1)=7400

Example 25
Fractosil®-bound N$^8$-8-Aza-2'-deoxyguanosine p-Nitrophenol (7 mg, 0.05 mmol) and N,N-dicyclohexylcarbodiimide (10 mg, 0.048 mmol) were added to a solution of the 3'-O-succinate (6) from Example 6 (30 mg, 0.04 mmol) in 1,4-dioxane/5% pyridine (1 ml). After the mixture had been stirred at room temperature for 2 hours, the filtrate from the solution was added to a suspension of Fractosil 200® (80 mg, 450 $\mu$mol/g; Merck) in DMF (1 ml). After triethylamine (100 $\mu$l) had been added, the mixture was shaken for 4 hours with acetic anhydride (20 $\mu$l) being added during this period. The polymeric support was filtered off, washed with 30 ml each of DMF, ethanol and ether, and dried in vacuo. In order to determine the yield of the polymer-bound nucleoside, the substance was taken up with 0.1 M p-toluenesulfonic acid (5 ml) in MeCN. The loading of the support was calculated, by UV spectrophotometry from the extinction at 498 nm (Dmt=70000), to be 64 $\mu$mol of 8-aza-2'-deoxyguanosine/g of Fractosil®.

Example 26
Solid-phase Synthesis of the Oligodeoxyribonucleotides Using the Phosphonate Method The oligodeoxyribonucleotide syntheses were carried out, on solid phase (CPG: ®Controlled Pore Glass) and on a 1 $\mu$mol scale, using the phosphonate technique and employing a 380 B DNA synthesizer (Applied Biosystems, Weiterstadt), with the DNA fragment being synthesized in the 3'–5' direction. Here, the oxidation cycle (detritylation, coupling, capping and oxidation) followed a program which was developed for phosphonate chemistry [H. Köster, K. Kulikowsky, T. Liese, W. Heikens, V. Kohli, Tetrahedron 1981, 37, 363]. The base-protected oligonucleotide, which was also Dmt-protected on the 5'-hydroxyl group, was cleaved off from the support within 30 min using 25% aqueous ammonia. Following a further addition of aqueous ammonia (1 ml, 25%), the protective groups on the heterocycles were eliminated within 24 hours at 60° C. After having added a drop of triethylamine (prevention of the premature elimination of the 5'-OH protective group), the samples were concentrated to about 200 $\mu$l in a Speed Vac ®Concentrator. In this state, they keep for some months at −25° C.

Example 27
Solid-phase Synthesis of the Oligodeoxyribonucleotides Using the Phosphoramidite Method The oligodeoxyribonucleotide syntheses were carried out, on a 1 $\mu$mol scale, by means of the solid-phase phosphoramidite technique, on an automated 380 B DNA synthesizer (Applied Biosystems, Weiterstadt) using ®CPG (Controlled Pore Glass) or ®Fractosil to which the first nucleoside unit was bound by its 3' end. In this case, the following steps were carried out:

1. washing with abs. acetonitrile, 2. treating with 3% trichloroacetic acid in dichloromethane,
3. washing with abs. acetonitrile,
4. condensing with 10 μmol of 5'-O-dimethoxytrityl-nucleoside-3'-β-cyanoethyl phosphite-diisopropyl amidite and 50 μmol of tetrazole in 0.3 ml of abs. acetonitrile,
5. washing with acetonitrile,
6. capping with 20% acetic anhydride in THF containing 40% lutidine and 10% dimethylaminopyridine,
7. washing with acetonitrile,
8. oxidizing with iodine (1.3 g in THF/water/pyridine; 70:20:5=v:v:v).

Steps 1 to 8, termed a DNA reaction cycle below, were repeated in order to construct the oligonucleotide which corresponded to the sequence to be synthesized, with the 5'-O-dimethoxytrityl(nucleoside base)-3'-β-cyanoethyl phosphite-diisopropylamidite corresponding to the sequence being in each case employed in step 4. Once the synthesis is complete, working-up takes place as described in Example 8.

Example 28
Synthesis of d(Cz$^8$GCGCG)

The synthesis was carried out as described in Example 25, proceeding from CPG-bound 5'-O-dimethoxytrityl-2'-deoxyguanosine. The first three nucleotide addition steps are carried out using commercially available 5'-O-dimethoxytrityl(nucleoside base)-3'-H-phosphonates. In order to introduce the 8-aza-2'-deoxyguanosine, 3'-[2-deoxy-5-O-(4,4'-dimethoxytrityl)-β-D-erythropentofuranosyl]5-{[(dimethylamino)methylidene]amin}-3H-1,2,3,-triazolo[4,5-d]pyrimidin-7-(6H)-one 3'-(triethylammonium phosphonate) (4) from Example 4 was used in the fourth condensation cycle.

Example 29
Synthesis of d(Cz$^8$GCz$^8$GCG)

The synthesis was carried out in a manner analogous to that described in Example 28, with 3-[2-deoxy-5-O-(4,4'-dimethoxytrityl)-β-d-erythropentofuranosyl]5-{(dimethylamino)methylidene]amino}-3H-1,2,3-triazolo[4,5-d]-pyrimidin-7-(6H)-one 3'-(triethylammonium phosphonate) (4) from Example 4 being in each case employed in the second and fourth condensation cycle in order to introduce the 8-aza-2'-deoxyguanosine.

Example 30
Synthesis of d(GCz$^8$GCGC)

The synthesis was carried out in a manner analogous to that described in Example 29, proceeding from a CPG support which was loaded with cytidine, with 3-[2-deoxy-5-O-(4,4')-dimethoxytrityl)-β-D-erythropentofuranosyl]5-{](dimethylamino)methylidene]amino}-3H-1,2,3 -triazolo-[4,5-d]pyrimidin-7-(6H)-one 3'-(triethylammonium phosphonate) (4) from Example 4 being employed in the third condensation cycle in order to introduce the 8-aza-2'-deoxyguanosine.

Example 31
Synthesis of d(Tz$^8$GGGGT)

The synthesis was carried out in an analogous manner to that described in Example 28, proceeding from CPG-bound 5'-O-dimethoxytritylthymidine, with 3-[2-deoxy-5-O-(4,4'-dimethoxytrityl)-β-D-erythropentofuranosyl]5-{[(dimethylamino)methylidene]amino}-3H-1,2,3-triazolo-[4,5-d]pyrimidin-7-(6H)-one 3'-(triethylammonium phosphonate) (4) from Example 4 being used in the fourth condensation cycle to introduce the 8-aza-2'-deoxyguanosine.

Example 32
Synthesis of d(TGz$^8$GGGT)

The synthesis was carried out in an analogous manner to that described in Example 30, proceeding from CPG-bound 5'-O-dimethoxytritylthymidine, with 3-[2-deoxy-5-O-(4,4'-dimethoxytrityl)-β-D-erythropentofuranosyl]5-{[(dimethylamino)methylidene]amino}-3H-1,2,3-triazolo-[4,5-d]pyrimidin-7-(6H)-one 3'-(triethylammonium phosphonate) (4) from Example 4 being used in the third condensation cycle in order to introduce the 8-aza-2'-deoxyguanosine.

Example 33
Synthesis of d(Tz$^8$Gz$^8$Gz$^8$Gz$^8$GT)

The synthesis was carried out in an analogous manner to that described in Example 30, proceeding from CPG-bound 5'-O-dimethoxytritylthymidine, with 3-[2-deoxy-5-O-(4,4'-dimethoxytrityl-β-D-erythropentofuranosyl]5-{[(dimethylamino)methylidene]amino}-3H-1,2,3-triazolo-[4,5-d]pyrimidin-7-(6H)-one 3'-(triethylammonium phosphonate) (4) from Example 4 being in each case used in condensation cycles 1 to 4 in order to introduce the 8-aza-2'-deoxyguanosine.

Example 34
Synthesis of d(GTAz$^8$GAATTCTAG)

The synthesis was carried out as described in Example 26, proceeding from CPG-bound 5'-O-dimethoxytrityl-2'-deoxyguanosine. 3-[2-Deoxy-5-O-(4,4'-dimethoxytrityl)-β-D-erythropentofuranosyl]5-{[(dimethylamino)methylidene]-amino}-3H-1,2,3-triazolo[4,5-d]pyrimidin-7-(6H)-one 3'-(trimethylammonium phosphonate) (4) from Example 4 was used in the eighth condensation cycle in order to introduce the 8-aza-2'-deoxyguanosine.

Example 35
Purification of the trityl-protected and deprotected oligonucleotides using HPLC.

The Dmt-protected oligomers were purified by HPLC on RP-18 silica gel (eluent system I), in a first purification step, and evaporated to dryness in vacuo at 40° C. A subsequent, 20-minute treatment with 250 μl of 80% acetic acid resulted in the elimination of the 5'-trityl group. In a second purification step, the oligomers, which were now completely deprotected, were purified for a second time by RP-18 HPLC (eluent system II). The combined main zones were evaporated and the residue was dissolved in approximately 500 μl of water; this solution was then desalted through a short RP-18 column (eluent system III). Following lyophilization, the oligomers (5–20 A$_{260}$ units) were taken up in 100 μl of water, and these solutions were stored at −25° C.

Use was made of the following eluent systems composed of:

0.1M triethylammonium acetate, pH 7.0/5% acetonitrile (A)

acetonitrile (B)
water (C)
methanol/water (3:2) (D)

I: 20 min (0–20% B) in A
II: 20 min (15–40% B) in A
III: 15 min C, 10 min D
IV: 100% A The oligomers were observed to have the following retention times:

| Oligomer | Example | Retention time (min) | Eluent |
|---|---|---|---|
| d(Cz$^8$GCGCG) | 10 | 15.1(12.5) | I(II) |
| d(Cz$^8$GCz$^8$GCG) | 11 | 15.8(12.9) | I(II) |
| d(GCz$^8$GCGC) | 12 | 15.5(12.5) | I(II) |
| d(Tz$^8$GGGGT) | 13 | 13.4(12.2) | I(II) |
| d(TGz$^8$GGGT) | 14 | 13.5(12.1) | I(II) |
| d(Tz$^8$Gz$^8$Gz$^8$GZ$^8$GT) | 15 | 13.6(12.4) | I(II) |
| d(GTAz$^8$GAATTCTAG)* | 16 | 15.0(12.4) | I(II) |

*(SEQ. ID. NO. 30)

Example 36
Characterization of the Oligodeoxyribonucleotides by Means of Enzymic Hydrolysis 0.2 $A_{260}$ units of the oligomers were dissolved in 0.1 M tris/HCl buffer (pH 8.3, 200 µl) and incubated with snake venom phosphodiesterase (EC 3.1.4.1, *Crotallus durissus*, Boehringer Mannheim; 6 µg) at 37° C. for 45 min, and with alkaline phosphatase (EC 3.1.3.1, calf liver, Boehringer Mannheim; 2 µg) at 37° C. for 30 min. The hydrolysis products were detected at 260 nm using reverse-phase HPLC (RP-18, eluent IV). The composition of the oligodeoxyribonucleotides was quantified using the peak areas and the extinction coefficients of the nucleosides ($\epsilon_{260}$: dA 15400, dC 7300, dG 11700, dT 8800, $z^8G_d$ 12000).

Example 37
Determination of the Enzymic Hypochromicity

The UV absorption at 260 nm of approximately 0.2 $A_{260}$ units of the oligomers was determined in 0.1 M tris/HCl buffer (pH 8.3, 200 µl) before and after adding snake venom phosphodiesterase (10 µg). Taking into consideration the absorption of the enzyme, the hypochromicity is given by the relationship:

$$H_{enzym.}=[(\Sigma_{monomer}-\Sigma_{oligomer})(\Sigma_{monomer})^{-1}]\times 100$$

Example 38
UV-Spectroscopic and CD-Spectroscopic Determinations of the $T_m$ Values, and Calculation of the Thermodynamic Data The $T_m$ values of the oligomers were determined using a Cary 1 UV/vis spectrophotometer (Varian, Melbourne, Australia). The temperature was varied linearly by 0.5° C. or 1.0° C. per minute. For investigating the melting temperature, oligomer concentrations of between 0.2–0.8 $A_{260}$ units in 1 ml of 60 mM of sodium cacodylate buffer (pH 7.5, 1 M NaCl, 100 mM $MgCl_2$) were used. In the experiments carried out on the nonself-complementary oligonucleotides, the single-strand concentration was 0.2–0.6 OD. The melting hypochromicity in % is obtained from the change in absorption before and after melting, in accordance with the following equation:

$$H_{melt}=[(A_e-A_t)A_e^{-1}]\times 100$$

The melting curves were analysed using a program based on a two-state model (stacked/unstacked) in accordance with the equation:

$$lnK=ln[(E^S-E)/(E^U-E)]=S/R-H/RT$$

where E=absorption at the relevant wavelength, S=stacked and U=unstacked. The temperature-dependent CD spectra were plotted on a Jasco 600 spectropolarimeter, using a temperature-regulatable quartz cuvette, in a wavelength range of 200–350 nm. The temperature was increased in internals of 5–10° C. in a range of 5–80° C., in concentrations of 3–15 µM in 60 mM Na cacodylate buffer, and also with 0.1 M, 1 M and 4 M NaCl.

Example 39
$T_m$ values and hypochromicity data for duplex formation a)

| Oligomer | Tm [° C.] | Hypochromicity [%] |
|---|---|---|
| d(CGCGCG) | 45 | 22 |
| d(GCGCGC) | 45 | 29 |
| d(Cz$^8$GCGCG) | 49 | 23 |
| d(Cz$^8$GCz$^8$GCG) | 52 | 21 |
| d(GCz$^8$GCGC) | 47 | 27 | a) Measured in 1 M NaCl, 100 mM $MgCl_2$, 60 mM cacodylate buffer, pH 7.0.

Example 40
Testing for Nuclease Stability 10 nmol of the oligonucleotide to be investigated are dissolved in 450 µl of 20% fetal calf serum in RPMI medium and 50 ml of doubly distilled water, and this solution is incubated at 37° C. 10 µl samples for gel electrophoresis and 20 µl samples for HPLC are then removed immediately and after 1, 2, 4, 7 and 24 hours, with these samples then being treated with 5 µl or 10 µl, respectively, of formamide to terminate the reaction and then being heated at 95° C. for 5 minutes. For the gel electrophoresis, the samples are loaded onto a 15% polyacrylamide gel (2% BIS), which is then developed at approximately 3000 volt hours. The bands are visualized by silver staining. For the HPLC analysis, the samples are injected into a Gene-Pack Fax HPLC column (Waters/Millipore) and chromatographed at 1 ml/min using from 5 to 50% buffer A in B (buffer A: 10 mM sodium dihydrogen phosphate, 0.1 M NaCl in acetonitrile/water 1:4 (v:v), pH 6.8; buffer B: as A, but containing 1.5 M NaCl.

Example 41
Testing for Antiviral Activity

The antiviral activity exerted by the test substances against various herpes viruses which are pathogenic to humans is investigated in a cell culture test system. For the experiment, monkey kidney cells (Vero, 2×10$^5$/ml) in serum-containing Dulbecco's MEM (5% fetal calf serum, FCS) are sown in 96-well microtiter plates, and incubated at 37° C. and 5% $CO_2$ for 24 h. The serum-containing medium is then sucked off and the cells are flooded twice with serum-free Dulbecco's MEM (-FCS). Prior to use, the test substances are diluted in $H_2O$ to a concentration of 600 µM and stored at −18° C. For the test, further dilution steps are carried out in Dulbecco's minimal essential medium (MEM). In each case, 100 μl of the individual test substance dilutions are added to the rinsed cells together with 100 μl of serum-free Dulbecco's MEM (-FCS). After having been incubated at 37° C. and 5% $CO_2$ for 3 h, the cells are infected with herpes simplex virus type 1 (ATCC VR733, HSV-1 F strain) or with herpes simplex virus tupe 2 (ATCC VR734, HSV-2 G strain) in concentraitons at which the cell lawn is completely destroyed within the space of 3 days. In the case of HSV-1, the magnitude of the infection os 500 plaque-forming units (PFU) per well, and in the case of HSV-2 350 PFU/well. The experimental samples then contain test substance in concentrations of from 80 μM to 0.04 μM in MEM, supplemented with 100 U/ml penicillin G and 100 mg/l streptomycin. All experiments are carried out in duplicate with the exception of the controls, eight of which are carried out per plate. The experimental samples are incubated at 37° C. and 5% $CO_2$ for 17 h. The cytotoxicity of the test substances is determined, after a total incubation time of 20 h, by microscopic assessment of the cell cultures. The highest preparation concentration which fails to elicit any microscopically recognizeable cell damage under the given experimental conditions is designated the maximum tolerated dose (MTD). After that, FCS is added to a final concentration of 4%, and the plates are incubated for a further 55 h at 37° C. and 5% $CO_2$. The untreated infection controls then exhibit a complete cytopathic effect (CPE). Once the cell cultures have been assessed microscopically, they are then stained with neutral red using the vital staining method of Finter (1966). The antiviral activity of a test substance is defined as the minimum inhibitory concentration (MIC) which is required in order to protect 30–60% of the cells from the cytopathic effect due to the virus.

Abbreviations

| | |
|---|---|
| A | adenosine |
| bz | benzoyl |
| br. | broad |
| calc. | calculated |
| CD | circular dichroism |
| d | doublet |
| dG | 2'-deoxyguanosine |
| dA | 2'-deoxyadenosine |
| dC | 2'-deoxycytidine |
| dT | 2'-deoxythymidine |
| DEPC | diethyl pyrocarbonate |
| DMA | dimethylacetamide |
| ($D_6$)DMSO | dimethyl sulfoxide, deuterated 6 times |
| DMF | dimethylformamide |

-continued

| | |
|---|---|
| DNA | deoxyribonucleic acid |
| Dmt | 4,4'-dimethoxytrityl, (4,4'-dimethoxytriphenyl-methyl) |
| EDTA | ethylenediamine tetraacetate |
| EtOAc | ethyl acetate |
| $Et_3N$ | triethylamine |
| FC | flash chromatography |
| G | free enthalpy |
| h | hour |
| H | duplex formation enthalpy |
| HPLC | high pressure liquid chromatography |
| Hyp. | hypochromicity |
| I | inosine |
| ibu | isobutyryl |
| J | coupling constant |
| $K_m$ | Michaelis-Menten constant |
| M.p. | melting point |
| NMR | nuclear magnetic resonance |
| PAGE | polyacrylamide gel electrophoresis |
| PCR | polymerase chain reaction |
| ppm | parts per million |
| 2-P-OH | isopropanol |
| $R_f$ | retention in TLC relative to the eluent front |
| RNA | ribonucleic acid |
| RP | reverse phase |
| R.T. | room temperature |
| s | singlet |
| S | duplex formation entropy |
| SVPD | snake venom phosphodiesterase |
| t | triplet |
| TBAF | tetrabutylammonium fluoride |
| TBC | triethylammonium bicarbonate |
| TEP | triethylammonium phosphonate |
| TLC | thin layer chromatography |
| Tms | tris(1-methylethyl)silyl |
| Tris | tris(hydroxymethyl)aminomethane |
| $T_m$ | oligomer melting temperature |
| U | uridine |
| UV | ultraviolet |
| $v_{max}$ | maximum reaction velocity |
| $z^8A$ | 8-azaadenosine |
| $z^8G$ | 8-aza-2'-deoxyguanosine |
| λ | wavelength |
| ε | molar extinction coefficient |

We claim:

1. An oligonucleotide of the formula I

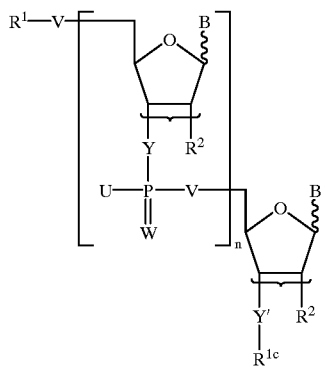

(I)

and the physiologically tolerated salts thereof, in which $R^1$ is hydrogen, $C_1$–$C_{18}$-alkyl, $C_2$–$C_{18}$-alkenyl, $C_2$–$C_{18}$-alkynyl, $C_2$–$C_{18}$-alkylcarbonyl, $C_3$–$C_{19}$-alkenylcarbonyl, $C_3$–$C_{19}$-alkynylcarbonyl, $(C_6$–$C_{14})$-aryl-$(C_1$–$C_8)$-alkyl, a protective group which is customary in nucleotide chemistry, or a radical of the formula IIa

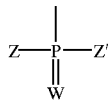

(IIa)

$R^{1a}$ is hydrogen, $C_1$–$C_{18}$-alkyl, $C_2$–$C_{18}$-alkenyl, $C_2$–$C_{18}$-alkynyl, $C_2$–$C_{18}$-alkylcarbonyl, $C_3$–$C_{19}$-alkenylcarbonyl, $C_3$–$C_{19}$-alkynylcarbonyl, $(C_6$–$C_{14})$-aryl-$(C_1$–$C_8)$-alkyl, or a radical of the formula IIb

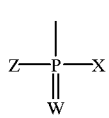

(IIb)

$R^2$ is hydrogen, hydroxyl, $C_1$–$C_{18}$-alkoxy, $C_1$–$C_6$-alkenyloxy, halogen, azido or $NH_2$;

a is oxy or methylene;

n is an integer from 3 to 99;

W is oxo, thioxo or selenoxo;

V is oxy, sulfanediyl or imino;

Y is oxy, sulfanediyl, imino or methylene;

Y' is oxy, sulfanediyl, imino, $(CH_2)_m$ or $V(CH_2)_{m'}$ in which m is an integer from 1 to 18;

X is hydroxyl or mercapto;

U is hydroxyl, mercapto, SeH, $C_1$–$C_{18}$-alkoxy, $C_1$–$C_{18}$-alkyl, $C_6$–$C_{20}$-aryl, $(C_6$–$C_{14})$-aryl-$(C_1$–$C_8)$-alkyl, $NHR^3$, $NR^3R^4$ or a radical of the formula III $$(OCH_2CH_2)_pO(CH_2)_qCH_2R_5 \qquad (III)$$

in which $R^3$ is $C_1$–$C_{18}$-alkyl, $C_6$–$C_{20}$-aryl, $(C_6$–$C_{14})$-aryl-$(C_1$–$C_8)$-alkyl, or 2-$(CH_2)_c$-$(NH(CH_2)_c)_d$—$NR^6R^6$, in which c is an integer from 2 to 6 and d is an integer from 0 to 6, and $R^6$ are, independently of each other, hydrogen or $C_1$–$C_6$-alkyl or $C_1$–$C_4$-alkoxy-$C_1$–$C_6$-alkyl;

$R^4$ is $C_1$–$C_{18}$-alkyl, $C_6$–$C_{20}$-aryl or $(C_6$–$C_{10})$-aryl-$(C_1$–$C_8)$-alkyl, or, in the case of $NR^3R^4$, is, together with $R^3$ and the nitrogen atom carrying them, a 5–6-membered heterocyclic ring which can additionally contain a further heteroatom selected from O, S and N, p is an integer from 1 to 100, q is an integer from 0 to 22, $R^5$ is hydrogen or a functional group;

Z and Z' are, independently of each other, hydroxyl, mercapto, SeH, $C_1$–$C_{22}$-alkoxy, —O—$(CH_2)_b$—$NR^6R^7$, in which b is an integer from 1 to 6, and $R^7$ is $C_1$–$C_6$-alkyl, or $R^6$ and $R^7$, together with the nitrogen atom carrying them, form a 3–6-membered ring, $C_1$–$C_{18}$-alkyl, $C_6$–$C_{20}$-aryl, $(C_6$–$C_{14})$-aryl$(C_1$–$C_8)$-alkyl, $(C_6$–$C_{14})$-aryl-$(C_1$–$C_8)$-alkoxy, where aryl is also heteroaryl, and aryl is optionally substituted by 1, 2, or 3 identical or different radicals from the group carboxyl, amino, nitro, $C_1$–$C_4$-alkylamino, $C_1$–$C_6$-alkoxy, hydroxyl, halogen and cyano, $C_1$–$C_{18}$-alkylmercapto, $NHR^3$, $NR^3R^4$, a radical of the formula III or a group which favors intracellular uptake or which serves as the label of A DNA probe, or, when the olionucleotide analog hybridizes to the target nucleic acid, attacks the latter with binding, crosslinking or cleavage,and the curved bracket indicates that $R^2$ and the adjacent radical Y or Y' can be located either in the 2' and 3' positions or else, conversely, in the 3' and 2' positions, where each nucleotide can be present in its D or L configuration and the base B can be located in the α or β position, where B are, independently of each other, a base which is customary in nucleotide chemistry, where at least one B is a base of the formula IV

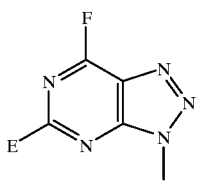

(IV)

in which E and F are, independently of each other, H, OH, or NH$_2$.

2. An oligonucleotide as claimed in claim 1, wherein the base B is located in the β position, the nucleotides are in the D configuration, R$^2$ is located in the 2' position and a is oxy.

3. An oligonucleotide as claimed in claim 1, wherein
R$^1$ is hydrogen, C$_1$–C$_6$-alkyl, or a radical of the formula IIa;
R$^{1a}$ is hydrogen, C$_1$–C$_6$-alkyl, or a radical of the formula IIb;
R$^2$ is hydrogen, C$_1$–C$_6$-alkoxy, C$_1$–C$_6$-alkenyloxy, or hydroxyl;
n is an integer from 4 to 39;
m is an integer from 1 to 6;
U is hydroxyl, mercapto, C$_1$–C$_6$-alkoxy, C$_1$–C$_6$-alkyl, NR$^3$R$^4$ or NHR$^3$, in which
R$^3$ is C$_1$–C$_8$-alkyl or methoxyethyl, and
B, W, V, Y, Y', X and Z have the meanings listed in claim 1.

4. An oligonucleotide as claimed in claim 1, wherein V, Y, and Y' are each independently oxy, sulfanediyl or imino.

5. An oligonucleotide as claimed in claim 1, wherein W is oxo or thioxo.

6. An oligonucleotide as claimed in claim 1, wherein U is hydroxyl, methyl or mercapto.

7. An oligonucleotide as claimed in claim 1, wherein at least one of R$^1$ and R$^{1a}$ is hydrogen.

8. A process for preparing an oligonucleotide of the formula (I), or a physiologically tolerated salt thereof, as claimed in claim 1, said process comprising condensing nucleotides, in each case containing a nucleotide base, one at a time, onto an appropriately derivatized support or onto a growing oligomer chain.

9. A process for preparing a pharmaceutical or a diagnostic agent, said process comprising mixing at least one oligonucleotide as claimed in claim 1 with a physiologically acceptable excipient and also, and optionally, with suitable aditives and/or auxiliary substances.

10. A pharmaceutical or a diagnostic agent, containing at least one oligonucleotide as claimed in claim 1, and optionally together with a physiologically acceptable excipient and/or auxiliary substances.

11. An oligonucleotide as claimed in claim 1, wherein R$^2$ is C$_1$–C$_6$ alkenyloxy.

12. An oligonucleotide as claimed in claim 11, wherein R$^2$ is C$_1$–C$_6$ allyloxy.

13. An oligonucleotide as claimed in claim 1, wherein R$^5$ is a functional group and is selected from hydroxyl, amino, C$_1$–C$_{18}$-alkylamino, COOH, CONH$_2$, COO(C$_1$–C$_4$)-alkyl and halogen.

14. An oligonucleotide as claimed in claim 1, wherein said bases customary in nucleotide chemistry are natural bases or unnatural bases or their prodrug forms.

15. An oligonucleotide as claimed in claim 14, wherein said natural bases are adenine, cytosine, thymine, guanine, uracil or hypoxanthine.

16. An oligonucleotide as claimed in clain 14, wherein said unnatural bases are purine, 8-azapurine, 2,6-diaminopurine, 7-deazaadenine, 7-deazaguanine, N$^4$N$^4$-ethanecytosine, N$^6$N$^6$-ethano-2,6-diaminopurine, pseudoisocytosine, 5-methylcytosine, 5-fluorouracil, 5-(C$_3$–C$_6$)-alkynyluracil, or 5-(C$_3$–C$_6$)-alkynylcytosine.

17. An oligonucleotide as claimed in claim 3, wherein
R$^1$ is C$_1$–C$_6$-alkyl;
R$^{1a}$ is C$_1$–C$_6$-alkyl;
R$^2$ is C$_1$–C$_6$-alkenyloxy or hydrogen;
n is an integer from 5 to 29;
m is 1;
U is hydroxyl or C$_1$–C$_6$-alkyl,
R$^3$ is C$_1$–C$_4$-alkyl.

18. An oligonucleotide as claimed in claim 17, wherein
R$^1$ is methyl;
R$^{1a}$ is methyl;
R$^2$ is C$_1$–C$_6$ allyloxy or hydrogen.

19. An oligonucleotide as claimed in claim 17, wherein R$^2$ is hydrogen.

* * * * *